(12) United States Patent
Medoff et al.

(10) Patent No.: US 8,821,508 B2
(45) Date of Patent: Sep. 2, 2014

(54) HOLDER/IMPACTOR FOR CONTOURED BONE PLATE FOR FRACTURE FIXATION

(75) Inventors: Robert J. Medoff, Kailua, HI (US); Alexander Y. Shin, Rochester, MI (US)

(73) Assignee: Trimed, Incorporated, Santa Clarita, CA (US)

( * ) Notice: Subject to any disclaimer, the term of this patent is extended or adjusted under 35 U.S.C. 154(b) by 0 days.

(21) Appl. No.: 13/598,234

(22) Filed: Aug. 29, 2012

(65) Prior Publication Data

US 2013/0046314 A1 Feb. 21, 2013

Related U.S. Application Data

(60) Continuation-in-part of application No. 13/103,658, filed on May 9, 2011, which is a division of application No. 12/114,916, filed on May 5, 2008, now Pat. No. 8,177,822.

(51) Int. Cl.
*A61B 17/58* (2006.01)
*A61B 17/92* (2006.01)
*A61B 17/80* (2006.01)
*A61B 17/17* (2006.01)

(52) U.S. Cl.
CPC ............... *A61B 17/809* (2013.01); *A61B 17/92* (2013.01); *A61B 2017/922* (2013.01); *A61B 17/1728* (2013.01); *A61B 17/8061* (2013.01); *A61B 2017/1775* (2013.01); *A61B 17/808* (2013.01); *A61B 17/1739* (2013.01)
USPC ......................................................... 606/99

(58) Field of Classification Search
USPC .................................................. 606/99, 297
See application file for complete search history.

(56) References Cited

U.S. PATENT DOCUMENTS

| 414,311 | A | * | 11/1889 | Hausmann | 433/1 |
|---|---|---|---|---|---|
| 1,338,376 | A | * | 4/1920 | Kocha | 81/163 |
| 4,201,213 | A | * | 5/1980 | Townsend | 606/174 |
| 5,385,570 | A | * | 1/1995 | Chin et al. | 606/170 |
| 7,037,308 | B2 | | 5/2006 | Medoff | |
| 7,267,678 | B2 | | 9/2007 | Medoff | |
| 7,338,497 | B2 | * | 3/2008 | Coon et al. | 606/99 |
| 8,177,822 | B2 | | 5/2012 | Medoff | |

(Continued)

OTHER PUBLICATIONS

Zuelzer, Wilhelm A., Fixation of Small But Important Bone Fragments With a Hook Plate, The Journal of Bone & Joint Surger, 1951; 33:430-436.

(Continued)

*Primary Examiner* — Christian Sevilla
(74) *Attorney, Agent, or Firm* — Patzik, Frank & Samotny Ltd.

(57) ABSTRACT

A bone fixation plate for fixation of fractures having a small terminal bone fragment, such as fractures of the distal radius. The plate includes an elongated body, and two hook members extending from a first end of the elongated body. A contoured region is configured to approximate the surface contour of the distal radius proximate the volar rim, the dorsal rim, or the radial arm. Each hook member is configured to provide subchondral support to a distal bone fragment, without causing shortening of the fragment into the metaphyseal bone, and without providing a bending torque directed to the base of the plate. The tooth members of the hook plate are preferably sharpened at their tips and edges to facilitate their impaction. A holder/impactor for gripping the radial hook plate, and for further facilitating impacting of the hook plate without the need to pre-drill pilot holes, is also provided.

9 Claims, 24 Drawing Sheets

(56) References Cited

U.S. PATENT DOCUMENTS

| | | |
|---|---|---|
| 2004/0092947 A1 | 5/2004 | Foley |
| 2005/0010228 A1 | 1/2005 | Medoff |
| 2011/0213420 A1 | 9/2011 | Medoff |

OTHER PUBLICATIONS

Weseley, M.S., et al., The Use of the Zuelzer Hook Plate in Fixation of Olecranon Fractures, The Journal of Bone & Joint Surger, 1976: 58:859-863.

Medoff, Robert J., Co-pending U.S. Appl. No. 13/598,206, filed Aug. 29, 2012 entitled "Contoured Bone Plate for Fracture Fixation Having Hook Members and Holder/Impactor for Same," having a common inventor and assignee in the present application.

Surgical Technique SCS Volar Distal Radius Plate System, Small Bone Innovations, Inc. Morrisville, Pennsylvania and SBi International, SAS, Peronnas, France, 2006.

Volar Bearing Plate Surgical Technique, TriMed, Inc., Valencia, California, 2011.

LCP Hook Plate 3.5. The Simple Fixation System for Tension Band Plating, Technique Guide, Synthes, Inc., West Chester, Pennsylvania, Jun. 2009.

* cited by examiner

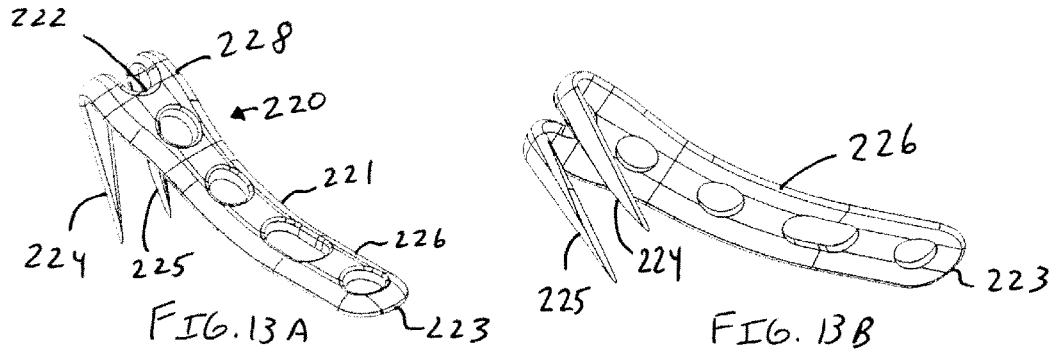
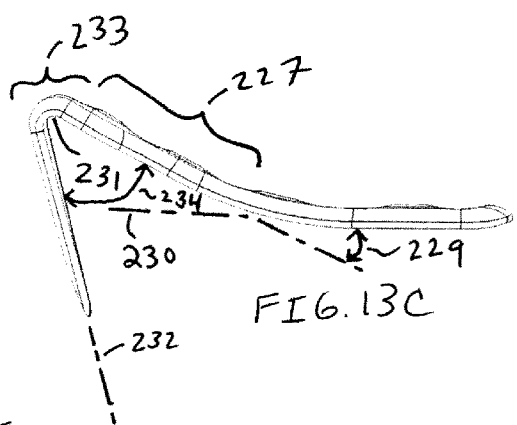
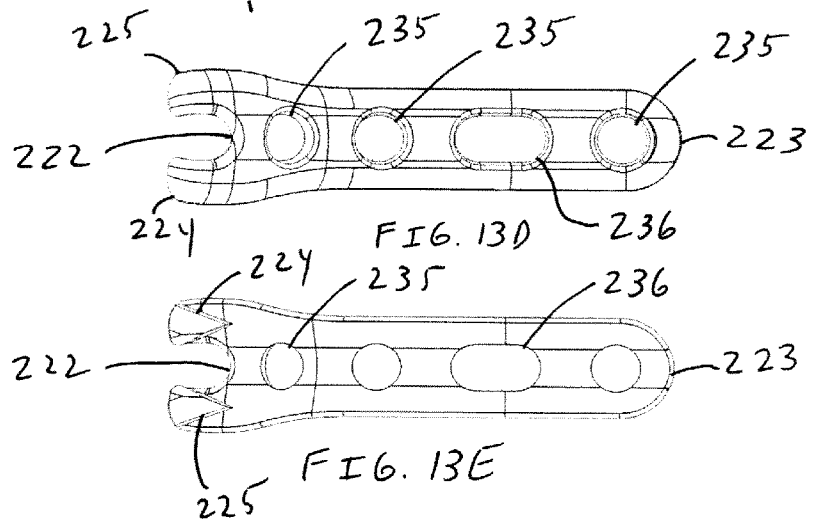

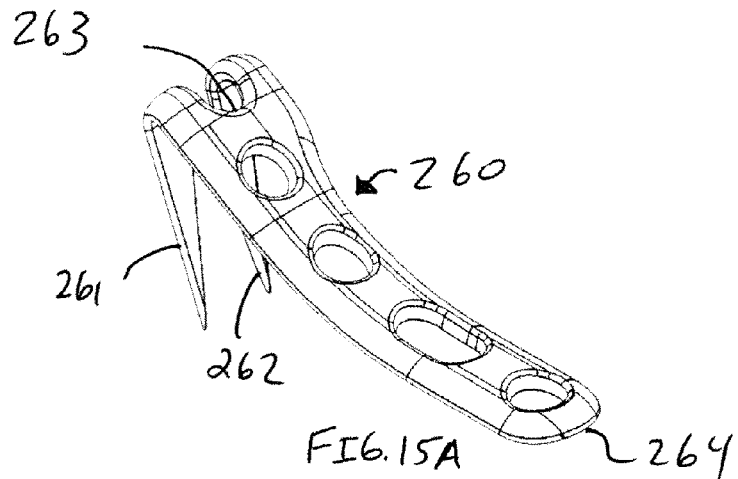
FIG. 15A
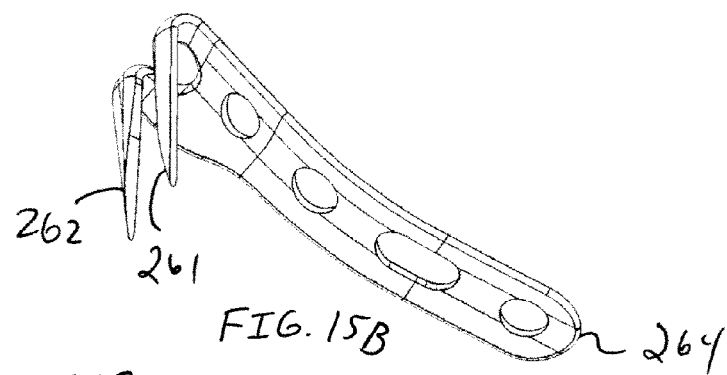
FIG. 15B
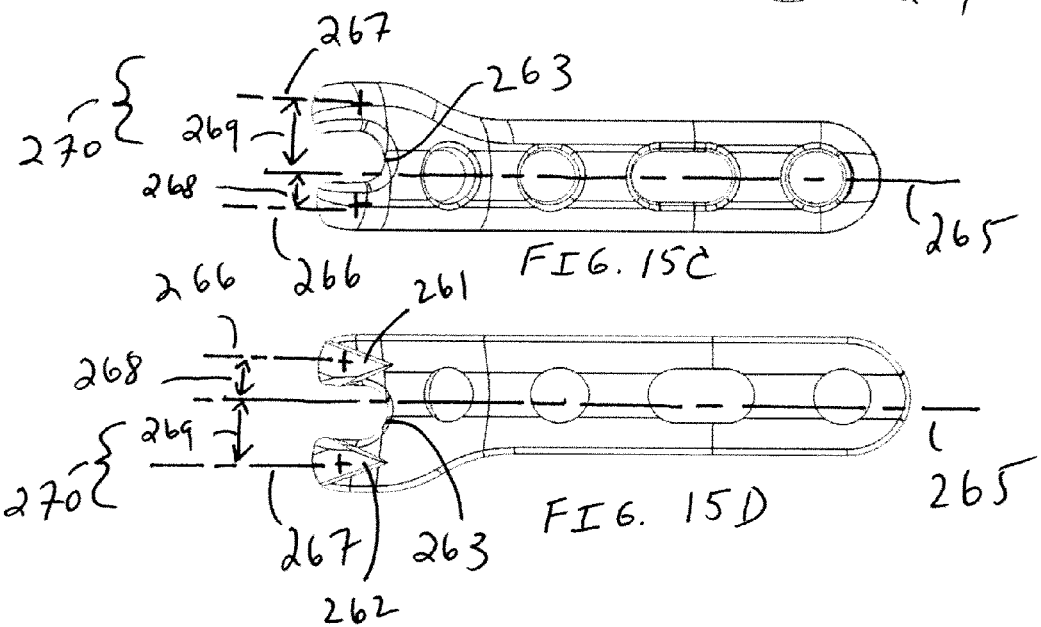
FIG. 15C
FIG. 15D

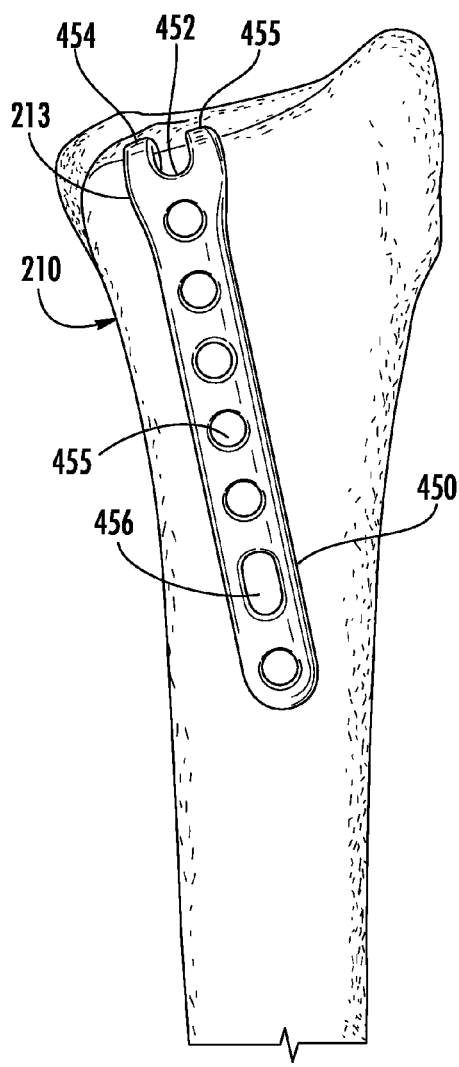
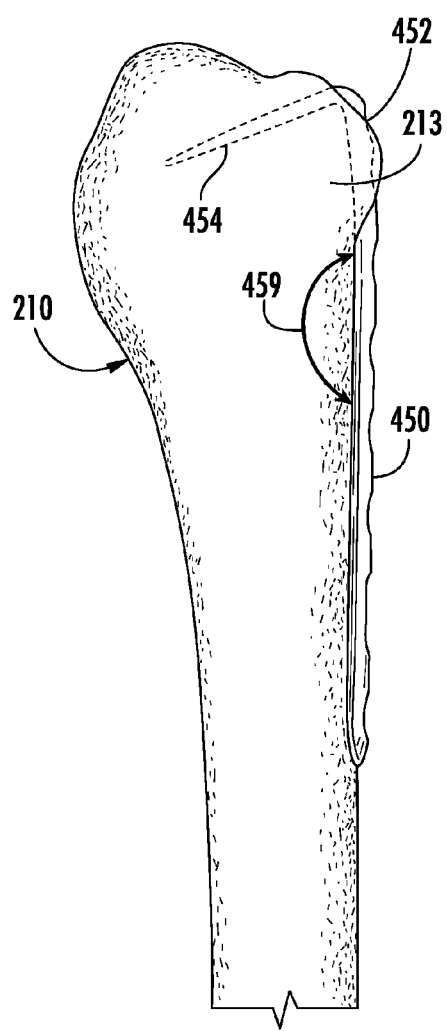
FIG. 24A                    FIG. 24B

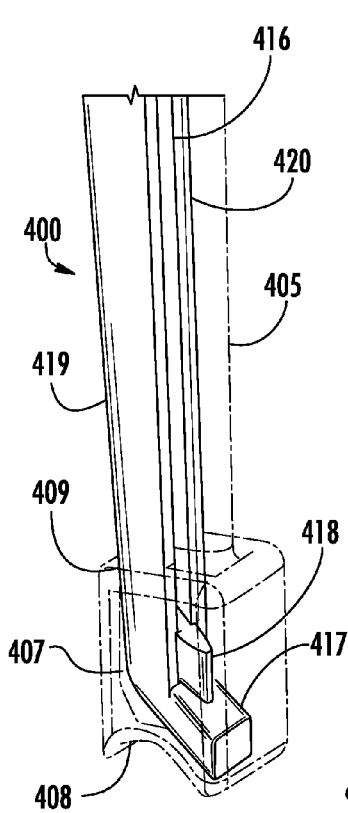 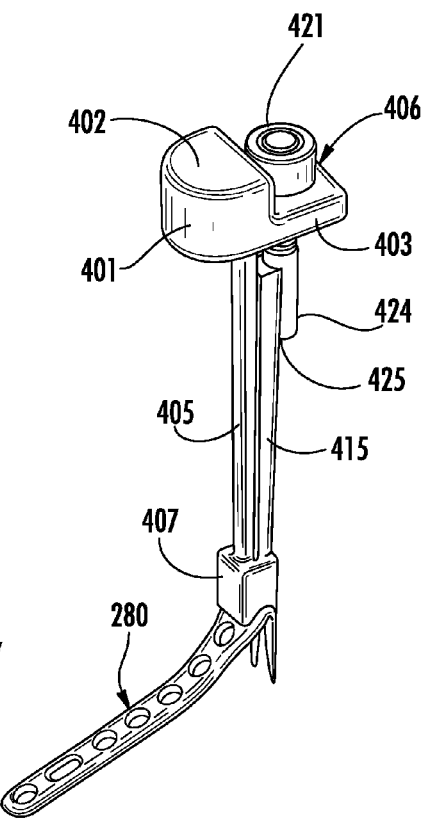 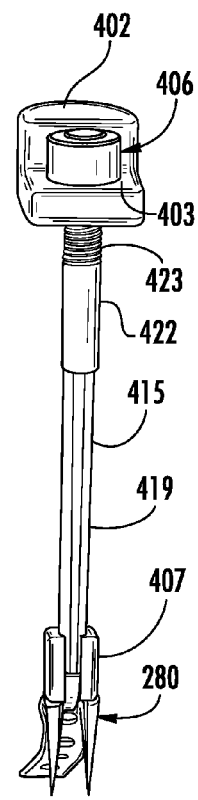
FIG. 27  FIG. 28  FIG. 29
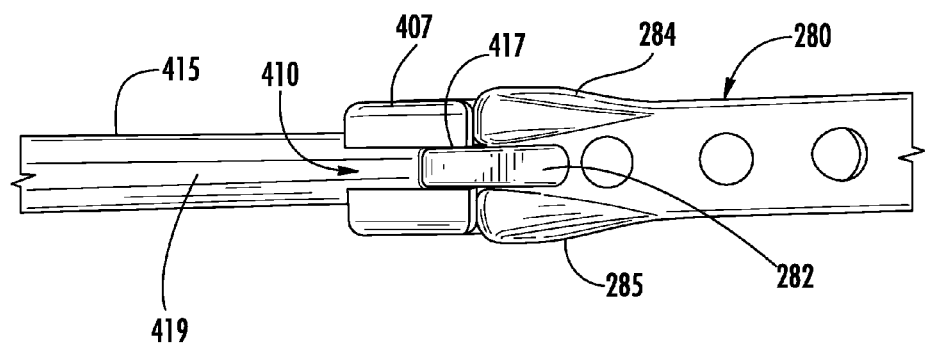
FIG. 30

HOLDER/IMPACTOR FOR CONTOURED BONE PLATE FOR FRACTURE FIXATION

CROSS-REFERENCE TO RELATED APPLICATIONS

This application is a continuation-in-part of pending U.S. patent application Ser. No. 13/103,658, filed May 9, 2011, the entirety of which is hereby incorporated by reference, which is a division of U.S. patent application Ser. No. 12/114,916 filed May 5, 2008, now U.S. Pat. No. 8,177,822, the entirety of which is hereby incorporated by reference.

BACKGROUND OF THE INVENTION

1. Field of the Invention

The present invention relates, in general, to the fixation of bone fractures and, more particularly, to the fixation of bone fractures having small fragments proximate a terminal end of a bone.

2. Description of Related Art

Plates and screws are well accepted techniques for fixation of fractures. The standard bone plate is a planar bar of material, usually metal, having circular and/or slotted holes through which bone screws are placed. The bone plate is used to span a fracture and fixation screws are placed through holes in the bone plate positioned on either side of the fracture to secure the bone fragments the plate.

One variation of the standard bone plate is to modify the configuration of the screw holes to help provide compression across the fracture as the screw is placed. Another variation is to include female threads within the perimeter of the bone plate's screw holes, engaging male threads on the head of the screw to lock the screw to the plate.

Difficulties in using bone plates may arise in certain fractures occurring relatively close to the end of a bone, creating a relatively small end fragment. In this situation, there may simply be not enough bone available in the end fragment to accommodate a sufficient number of screws to achieve secure fixation. As a result, a surgeon using a conventional bone plate may use a suboptimal number of screws, which can lead to postoperative failure.

One example of a fracture occurring relatively close to the end of a bone is a fracture of the lateral malleolus, the terminal portion of the fibula that is present on the outside of the ankle, occurring close to its tip. In such situations, only a very small distal fragment may be present, providing inadequate room for more than one or two screws to be placed. Moreover, since the deep portion of this bone is a part of the overall ankle joint, screws cannot be placed through both cortices, as is commonly practice with plate/screw techniques. Accordingly, the surgeon may be faced with the undesirable situation of having the patient leave the operating room with only one or two screws engaging a bone surface directly under a bone plate.

In the past, one technique surgeons have used in an attempt to provide enhanced fixation or grip of a small terminal bone fragment is to begin with a standard plate and cut the plate transversely across at its last screw hole. Using a pair of surgical pliers or other suitable instrument, the remaining bone plate material on opposing sides of the partially remaining hole is bent around the outer surface of the terminal bone fragment. To some degree, this helps supplement the tenuous fixation provided by only one or two screws in the small terminal fragment. However, this terminal bone fragment may still remain far from being well secured.

In another previous technique disclosed in "Use of Zuelzer Hook Plate in the Treatment of Olecranon Fractures" by Wesely, Barenfeld, and Eisenstein, The Journal of Bone & Joint Surgery, Volume 58-A, Issue No 6, September 1976, pages 859-863, a further modification of this technique is described in which a flat plate is pre-contoured with two hooks at one end. The hooks are bent so that they are parallel to the longitudinal axis of the flat plate. The plate is applied to a fractured bone such as the olecranon by manually pressing the hooks into the bone and fixing the plate to the bone surface with screws. Although this technique adds the theoretical advantage of penetration of the terminal fragment with the hooks, if this plate is applied to an anatomic site in which the bone flares out at the terminal end, since the hooks are parallel to the linear axis of the plate, as the hooks are impacted, the plate will not sit flush with the bone surface past the flare at the terminal end but rather come to lie in a position that sits off the bone. In addition, this technique does not address the problem of creating holes in the bone at the correct depth for engagement by the hooks, but rather relies on manual pressure on the plate to attempt penetration of the bone by the hooks at whatever level they happen to contact. As can be noted by the examples in this article, the hooks may fail to penetrate the bone resulting in less than satisfactory engagement and fixation of the terminal fragment by the hooks as well as prominence of the hooks in the soft tissue because of incomplete seating. Finally, since these implants have hooks that extend an equal distance from the end of the plate, this design does not allow completely seating of both hooks in the common situation in which the bone surface at the terminal end is at an angle to the plane that is perpendicular to the long axis of the bone.

Distal radius fractures (what is often meant when using the term 'wrist fracture') are common injuries. These fractures are often comminuted and unstable. It is of importance in addressing such fractures to restore a smooth, anatomic and congruent articular surface with enough stability so that it does not displace during healing. In other locations in the body one objective of internal fixation is to produce compression between stable and unstable fragments in order to promote healing. However, in the case of the distal radius fractures, fixation that would produce this type of compressive loads between the articular fragments and the shaft may result in migration of the fragments, loss of length, malunions and failure. For this reason, the tenets of internal fixation for distal radius fractures are different, aimed at achieving a stable anatomic reduction while maintaining the joint surface in space supported out to length.

Recently, surgical fixation has become the procedure of choice for many of these unstable distal radius fractures. One common method of fixation is to apply a plate to the volar surface of the radius, with a locked fixed angle support behind the bone under the articular surface. As load is applied to the end of the bone during healing, the fixed struts under the articular surface prevent setting of the articular surface into the soft bone at the end of the radius and loss of fracture reduction and length.

An early design that used this approach was the SCS plate, manufactured by Small Bone Innovations, Inc. This plate has four tines that are integrally formed with the plate and bent at a right angle to the plane of the predominant distal surface of the plate. These tines functioned as fixed posts. However, there are certain shortcomings to this design. First, since there are four posts integrally formed with the plate, a somewhat cumbersome drill guide apparatus is required to be applied to the bone in order to drill the holes for all four posts simultaneously. This requires that the surgeon reduce the fracture (restore all fragments in space to a position that reflected normal anatomy of the bone) and then maintain it in position while the drill guide was applied, then removed, and the plate then applied. This can be significantly difficult to achieve. Another shortcoming that arises from the use of four fixed posts is that the drill guide cannot generally be moved during the drilling of each of the four holes. In addition, the surgeon is required to simultaneously align each of the four drilled holes with the corresponding leading tips of each of the four tines in order to get the plate inserted. Since this plate was intended to be a single size approach to variable fracture patterns, fracture elements didn't always line up in the optimal position for insertion of the tines. In other words, this design lacks the flexibility often required to avoid placing tines directly through fracture lines (which can push fragments apart, contributing to instability). These issues can lead to inadequate fixation.

A variation of the foregoing technique replaces the tines with pegs or screws, insertable at fixed angles through the body of the plate. This design has the advantage of allowing a surgeon to apply the plate and individually drill each hole and insert each peg separately, thus avoiding the difficulties associated with inserting four tines into drilled pilot holes simultaneously. However, this design still remains a one size fits all solution, and lacks flexibility to line up fixation for some complex fracture patterns. In addition, this design still requires that the anatomy be restored along the articular surface and held in place in order to apply the plate.

Another variation of this design is a plate that has fixation pegs that can be directed at a variety of angles, and then angularly locked into the plate. One example is the Volar Bearing Plate, manufactured by TriMed, Inc. Although this approach adds further flexibility to the direction of the fixation pegs, it still requires the surgeon to restore and hold the anatomy while the fixation is taking place, which can sometimes be difficult to perform. In addition, this design does not solve the problem of avoiding the placement of pegs through fracture lines, since the relative position of the peg holes is fixed, and moving the entry of one peg by shifting the plate to a different location results in corresponding movement of the placement locations of all of the other associated pegs.

Generally volar fixation plates need to be thick in cross-section in order to provide sufficient material to allow enough internal threads in the holes in order to securely lock the cooperatively threaded peg to the plate (whether at a fixed or variable angle). Since it is known that thick implants close to the rim of the distal radius may often cause irritation and even rupture of important tendons and other vital structures nearby, existing volar generally plates do not extend to the distal rim. As a result, small fractures of the distal volar rim are often not be secured by these plate designs, which can result in the fragment flipping over the edge of the plate, potentially causing catastrophic loss of reduction and dislocation of the carpal bones of the wrist.

Another approach to fixation of complex fractures uses a fragment specific technique. Generally, this method consists of individually securing each fragment separately with a specific implant. This can overcome the requirement that the surgeon hold the entire reduction in place, since each fragment can be reduced and fixed one at a time. One common implant used for this technique utilizes small plates with small fixed angle pegs, screws, or pins for purchase of the unstable fragment. These implants require the fragment to be reduced, the plate applied, and then the holes prepared and drilled followed by insertion and locking of the pegs, screws, or pins. These multiple steps can be somewhat difficult and time consuming, and may be an objection to application of this technique.

Another type of fragment specific implant uses wire forms or buttressing pins that penetrate fragments and hold it out to length. For example, the Volar Buttress Pin, manufactured by TriMed, Inc., is an implant that can be used to extend over the volar or dorsal rim. This implant is low profile and accordingly is unlikely to interfere with adjacent tendons or other vital structures. The buttress pin penetrates the fragment for fixation. However the surgical technique for this type of implant does require pre-drilling the holes for insertion of the legs of the buttress pin. These steps can be difficult to perform, often requiring surgeons with above average ability and experience. In addition, since these types of implants are a type of bent wire, they lack the strength and rigidity of larger plates.

Hook plates are implants that have been used at other locations to address fixation of a small terminal fragment with little available osseous bone area to accommodate fixation screws. Although early designs such as the LCP Hook Plate manufactured by Synthes, Inc. wrap around the end of the bone, these types of implants do not achieve any internal purchase of the fragment to be secured, and may have very limited to no purchase overall, resulting in poor rotational stability and limited resistance to sideways drift of the terminal fragment.

The hook plates of the present invention, configured for application to the lateral malleolus or the olecranon, achieve fixation of terminal fragments with two 'teeth' that provide rigid internal purchase of the fragment. These hook plates provide for rigid fixation of the terminal fragment and angular or translational movement under the plate. In addition, this type of plate promotes compressive load across the fracture which is intended for treatment at these locations.

For fixation of the distal radius, however, the configuration of these types of hook plates is not optimal, especially for fractures involving the volar or dorsal rim. Since hook plates of the present invention configured for application to the lateral malleolus or the olecranon promote compression against the stable fragment, in the case of distal radius fixation this would cause shortening of the fragment into the metaphyseal bone, and thus loss of articular reduction. The use of such hook plates is counterintuitive thus contraindicated for this type of internal fixation.

Accordingly, it is an object of the present invention to provide a bone plate that adequately secures a small bone fragment at a terminal end of a bone.

It is a further object of the present invention to provide a bone plate that can be seated flush against a bone characterized by a flare at the terminal segment, yet sill providing full engagement of the small terminal fragment by complete seating of one or more hooks into bone. It is a further object of the present invention to provide a means to create pilot holes in the terminal fragment for engagement by the hooks in the plate such that the hook or hooks in the plate engage the bone at the correct depth and trajectory so as to direct the plate to advance both longitudinally as well as drop down against the surface of the bone as it is seated.

It is another object of the present invention to provide a design that has a contour that approximates the flare of the terminal segment of a bone as well as provides one or more hooks that are angled along an axis that approximates the best linear fit approximation of such flare.

It is another object of the present invention to provide an implant to rigidly hold bone fragments proximate the volar rim, dorsal rim, or other area proximate to the articular surface of the distal radius, and to provide subchondral support of the articular surface to prevent loss of length.

It is another object of the present invention to provide an implant that resists shortening of bone fragments and acts like a buttress to the distal fragments.

It is another object of the present invention to provide an implant that resists application of bending torque directed to the base of the plate.

It is another object of the present invention to provide an implant that can be impacted without the need to pre-drill pilot holes in the bone proximate the fracture site.

It is another object of the present invention to provide implants having tines, or toothed members, positioned at various locations and individualized to a specific pattern of an injury.

It is another object of the present invention to provide a holder/impactor to securely grip a bone plate to be implanted, and to provide a striking surface to permit the surgeon to impact the tines of the bone plate directly into the distal radius.

It is another object of the present invention to provide a drill guide facilitating accurate placement of a bone plate proximate a terminal end of a bone.

These and other objects and features of the present invention will become apparent in view of the present specification, drawing and claims.

BRIEF SUMMARY OF THE INVENTION

The present invention comprises a bone plate for fixing fractures having a small terminal fragment. The bone plate has an elongated body having a first end, a second end, a top surface, a bottom surface, and an angled or curved flared region disposed between the first end and the second end that can be described by a best fit first longitudinal axis. At least one hook member is provided proximate the first end and has a prong region having a second longitudinal axis. Moreover, the first longitudinal axis and the second longitudinal axis are substantially parallel to each other.

In one preferred embodiment of the present invention, the at least one hook member comprises a first hook member and a second hook member, with each of the first and second hook members having a prong region with a second longitudinal axis substantially parallel to the first longitudinal axis. The first hook member has a first curved region including a first apex, the second curved member has a second curved region including a second apex, and the distance between the second end and the first apex is greater than the distance between the second end and the second apex. In another preferred embodiment, the distance between the second end and the first apex is equal to the distance between the second end and the second apex.

Moreover, in a preferred embodiment, the elongated body includes a first region and a second region on opposing sides of the angled region, with the first region, angled region, and second region collectively form a surface substantially corresponding to the surface contour of the human fibula at the lateral malleolus. Other embodiments contemplated by the present invention may be formed with the angled region designed to conform to the contour of other sites of application in which the bone surface flares superficially at the terminal end, such as the olecranon, proximal ulna, proximal or distal humerus, medial malleolus, or similar bones. The elongated body preferably includes at least one bone screw accepting hole extending therethrough, and at least a portion of the bottom surface of the elongated body has a concave curvature. This concave curvature is dimensioned to substantially correspond to the surface curvature of the human fibula proximate the lateral malleolus. Moreover, the at least one hook member has a curved region curving from the elongated body proximate the first end, back towards the second end of the elongated body and terminating in the prong region.

The present invention also comprises a multiple barreled drill guide facilitating the drilling of at least two parallel holes at the distal end of a bone at the correct depth. The multiple barreled drill guide has a body, at least two sleeves coupled to the body in substantially parallel orientation relative to each other, with each sleeve having a first longitudinal axis, and an elongated positioning member extending from the body and having a second longitudinal axis. The first longitudinal axis may be angled relative to the second longitudinal axis such that, when the drill guide is positioned with the elongated positioning member disposed along a distal end of a human fibula and the sleeves abutting a terminal end of the fibula, the first longitudinal axis of each sleeve extends into the lateral malleolus of the fibula. In a preferred embodiment, this angle between the first longitudinal axis and the second longitudinal axis is approximately three degrees. In another preferred embodiment, the first longitudinal axis and second longitudinal axis are parallel.

The double barreled drill guide further includes a cooperating inner drill guide configured to releasably engage the multiple barreled drill guide. The inner drill guide includes an inner drill guide body, and at least two inner sleeves coupled to the inner drill guide body, with at least a portion of each of the inner sleeves being aligned by the inner drill guide body for axial insertion into at least a portion of a corresponding sleeve of the multiple barreled drill guide. In one variation of the inner drill guide, at least one of the inner sleeves includes an internal channel sized to accommodate a 0.9 mm Kirshner wire, with an outer diameter of 2.0 mm to fit in the double barreled guide which can accept a 2.0 mm drill.

The double barreled drill guide further includes a gauge configured to releasably engage the multiple barreled drill guide. The gauge has a gauge body, a first elongated member coupled to the gauge body and having a first end, a second elongated member coupled to the gauge body and having a second end. At least a portion of the first and second elongated members are aligned by the gauge body for axial insertion into at least a portion of a corresponding sleeve of the multiple barreled drill guide. Moreover, the first and second elongated members are of unequal length. The gauge further includes indicia disposed on the gauge body and indicating a current orientation of the gauge.

In other embodiments of the present invention, a hook plate is configured, upon implantation, to rigidly hold the volar or dorsal rim of the distal radius, and to provide subchondral support of the articular surface to prevent loss of length. This is achieved by configuring the hook plate to have a bottom curvilinear surface that coincides with the flare and surface geometry of either the volar or dorsal surface of the distal radius, respectively, with the plate terminating in two hooks to penetrate the volar or dorsal rim along the subchondral bone. These hooks do not angle back in line with the long axis of the bone, as in the case of hook plates of the present invention for addressing fractures of the lateral malleolus, but rather angle along the direction of the subchondral bone. These distal radius hook places are thus designed to resist shortening of the fragment and to act like a buttress, or support, for the distal bone fragments. Unlike other hook plates that are used to compress a fragment with bending torque on the hooks directed away from the plate, these implants are used to resist shortening and need to resist a bending torque directed to the base of the plate.

The radial hook plate in one embodiment uses hooks that are sharpened at their tips and at their leading edges. This allows the hooks to be simultaneously impacted like a nail or staple, and eliminates the steps of setting up a drill guide, drilling, removing the drill guide, finding the holes with both hooks and impacting. Rather, the implant can simply be applied and hammered into place. The surgeon simply applies the hooks in position, hammers the hooks along the subchondral surface, and applies the plate proximally to the shaft, reducing the fragment. Since the distal fixation elements or tooth members do not require a threaded hole, the thickness of the implant can be significantly reduced, thereby reducing the likelihood of irritation of tendons and other soft tissues. A holder/impactor instrument is provided to facilitate implantation and the precision of intended placement in the absence of pre-drilled pilot holes at the fracture site.

Moreover, depending upon the configuration of a particular fracture, the number and location of implants can be individualized to the specific pattern of the injury. For instance, two plates can be used side by side to individually fix fragments along the ulnar side and the radial side of the distal radius, including plates having left and right offset tines, or hook members, relative to a longitudinal axis of the hook plate. This allows the plate to be aligned with the long axis of the bone proximally where the bone is narrow, but still get the spread of fixation over a wider area distally where the bone is wider. Moreover, volar and dorsal plates can be combined, or volar, dorsal, and radial arm plates may be employed in various combinations. In this way, fixation can be easily customized to variation in the position of the fracture lines.

In certain embodiments of the distal radius hook plates, a second tier of subchondral fixation is provided by adding a fixed angle peg hole that is directed at an angle that extends between the axes of the hooks. This allows a third point of subchondral support in addition to the two hooks, acting like a cup behind the articular surface.

BRIEF DESCRIPTION OF THE SEVERAL VIEWS OF THE DRAWINGS

FIG. 13A is top perspective view of a 4-hole, neutral offset fracture fixation plate of the present invention, configured for volar application in the fixation of certain fractures of the distal radius;

FIG. 13B is a bottom perspective view of the fracture fixation plate of FIG. 13A;

FIG. 13C is a left side view of the fracture fixation plate of FIG. 13A;

FIG. 13D is a top plan view of the fracture fixation plate of FIG. 13A;

FIG. 13E is a bottom plan view of the fracture fixation plate of FIG. 13A;

FIG. 15A is top perspective view of a 4-hole, right offset fracture fixation plate of the present invention, configured for volar application in the fixation of certain fractures of the distal radius;

FIG. 15B is a bottom perspective view of the fracture fixation plate of FIG. 15A;

FIG. 15C is a top plan view of the fracture fixation plate of FIG. 15A;

FIG. 15D is a bottom plan view of the fracture fixation plate of FIG. 15A;

FIG. 24A is a top view of the 7-hole, neutral offset fracture fixation plate, shown impacted dorsally into a fractured distal radius and prior to final affixation;

FIG. 24B is a left side view of the 7-hole, neutral offset fracture fixation plate of FIG. 24A, shown impacted dorsally into a fractured distal radius and prior to final affixation;

FIG. 27 is a see-through view of a portion of the holder/impactor of FIG. 25 and showing, in particular, the foot member in its fully retracted position within the distal housing;

FIG. 28 is a top perspective view of the holder/impactor of FIG. 25, shown secured to a fracture fixation plate;

FIG. 29 is a front view of the holder/impactor of FIG. 25, shown secured to a fracture fixation plate;

FIG. 30 is a bottom plan view of a portion of the 7-hole, volar neutral offset fracture fixation plate of FIGS. 16A through 16C, shown secured to the holder/impactor of FIG. 25;

DETAILED DESCRIPTION OF THE INVENTION

Figure 1:
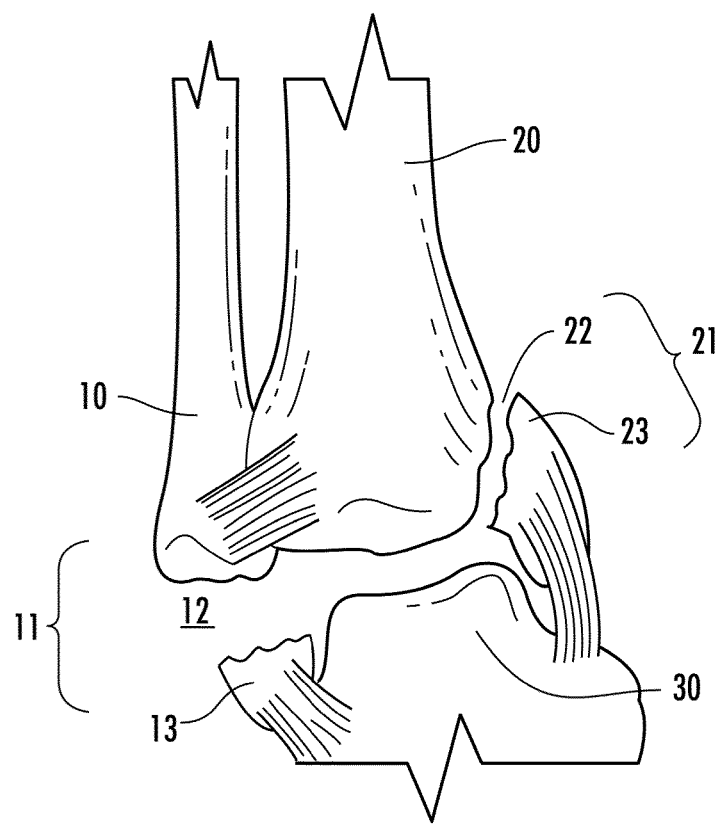
FIG. 1 is a simplified anterior view of a portion of the human right ankle, showing fractures of both the lateral malleolus of the fibula and medial malleolus of the tibia.

While several different embodiments of the present invention are described herein and shown in the various figures, common reference numerals in the figures denote similar or analogous elements or structure amongst the various embodiments.

A simplified anterior view of a portion of the right human ankle is shown in FIG. 1 as comprising fibula 10, tibia 20, and talus 30. Right fibula 10 is shown having a fracture of the lateral malleolus 11 thereof, creating a small terminal fragment 13 proximate fracture site 12. Simultaneously, right tibia 20 is shown having a fracture of the medial malleolus 21 thereof, creating a small terminal fragment 23 proximate fracture site 22.

Figure 2A:
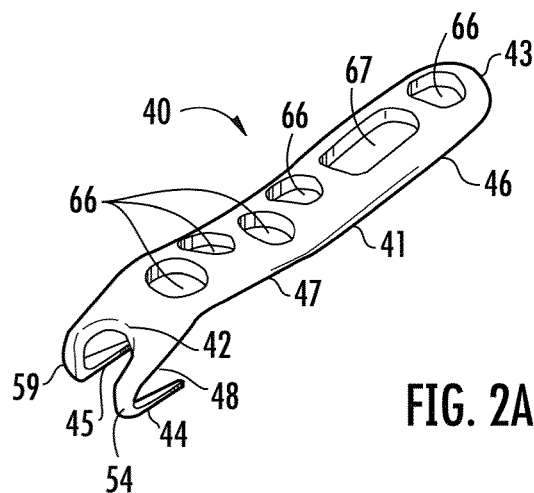
FIG. 2A is a perspective view of a 6-hole left offset fracture fixation plate of the present invention, configured for use in the fixation of certain fractures of the ankle.
Figure 2B:
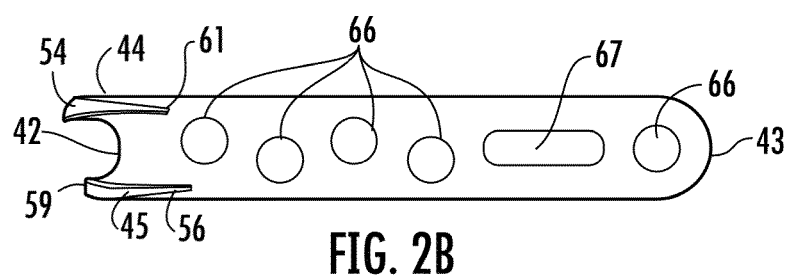
FIG. 2B is a bottom view of the 6-hole left offset fracture fixation plate.
Figure 2C:
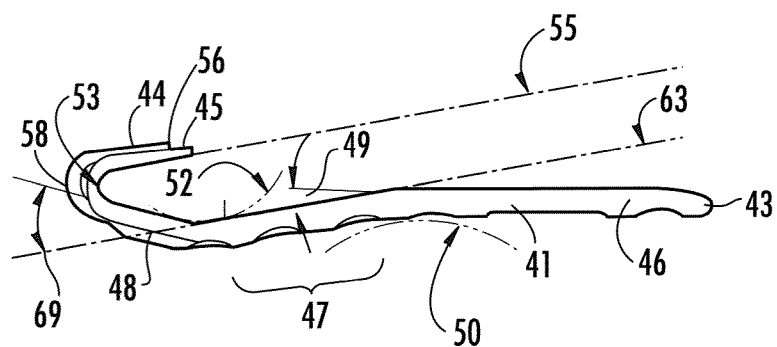
FIG. 2C is a right side view of the 6-hole left offset fracture fixation plate.
Figure 2D:
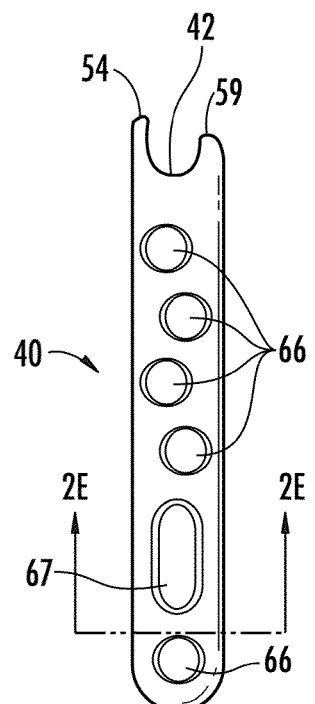
FIG. 2D is a top plan view of the 6-hole left offset fracture fixation plate.

A six-hole left offset bone plate 40 of the present invention, configured for use in conjunction with fractures of the lateral malleolus, is shown in FIGS. 2A through 2F as comprising an elongated body 41, having a first end 42 proximate first hook member, or tooth member 44 and second hook member, or tooth member 45. Elongated body 41 includes a first region 48 proximate first end 42, a second region 46 proximate a second end 43, and an intermediate, angled, or "flared" region 47 disposed between first region 48 and second region 46. Elongated body 41 includes a plurality of apertures extending therethrough for use in conjunction with conventional bone screws, including five circular holes 66, and one slotted hole 67. As best seen in FIGS. 2B and 2D, circular holes 66 are in a collectively staggered off-center orientation, relative to a longitudinal axis of elongated body 41, while slotted hole 67 is centered along this longitudinal axis. Moreover, and as best seen in FIG. 2A, slotted hole 67 and each circular hole 66 includes an associated countersunk, beveled perimeter, relative to the top surface of elongated body 41, facilitating the frusto-conical heads of conventional bone screws to be fully seated against, and hence in securing engagement with, an associated hole upon implantation.

As best seen in FIG. 2C, angled region 47 is generally defined and created by the presence of first radius of curvature 52 relative to the bottom surface of bone plate 40 proximate the juncture of substantially linear first region 48 and substantially linear angled region 47; together with the presence of second radius of curvature 50 relative to the top surface of bone plate 40 proximate the juncture of substantially linear second region 46 and angled region 47. The length of the linear angled region 47 and the inclination defined as the angle 49 between a line 63 parallel to linear angled region 47 with the longitudinal axis of the elongated body 41, substantially match the length and inclination of the flare of the associated bone requiring fracture fixation. It should be noted that substantially linear first region 48 may in fact be a curved surface that may be approximated by a best fit inclination angle 49. As a result, the bottom surface of elongated body 41 of bone plate 40 has an overall longitudinal contour which substantially corresponds to the flared profile of the distal end of the human fibula proximate the lateral malleolus. These values, including the lengths of angled region 47, first region 48, and second region 46, radii of curvature 50 and 52, and angles 49 and 69, may be modified during the manufacturing process to create a hooked bone plate specifically tailored for other sites of application having a bone surface flare superficially proximate the terminal end, such as the medial malleolus, olecranon, proximal ulna, proximal femur, proximal fifth metatarsal, proximal or distal humerus, or other such sites of application.

In one preferred embodiment, the length, contour and relative angling of linear angled region 47, relative to first region 48 and second region 46, is designed and to match the flare of the surface contour of the site of application using an electronically scanned or mathematical three-dimensional model of the site of application, such as the lateral malleolus or olecranon as examples. In particular, a three-dimensional mathematical model of a particular bone having a flared surface region proximate its terminal end is created, using a three-dimensional scan of either an actual human bone or an artificial model of a human bone, or a three-dimensional model created entirely by computer. Computer aided drafting software is then used in conjunction with this three-dimensional mathematical model of the bone to create a bone plate of the present invention having a back surface profile of angled region 47, first region 48 and second region 46 such that, when the prong members are impacted proximate the terminal end of the bone, this back surface profile substantially corresponds to the adjacent flared contour of the bone, such that the bone plate rests substantially adjacent the bone.

Referring to FIG. 2C, in a preferred embodiment of a six-hole hook plate of the present invention, wherein the instrument has an overall length of approximately 2.874 inches, and a length of elongated body 41 between first end 42 and second end 43 of approximately 2.278 inches, first angle of curvature 52 has a radius of approximately 0.380 inches, yielding a first curved bend angle 69 of approximately 25° at the junction of the bottom surface of angled region 47 and the bottom surface of first region 48 of elongated body 41. Moreover, for this embodiment of a six-hole hook plate of the present invention, second angle of curvature 50 has a radius of approximately 0.500 inches, yielding a second curved bend angle 49 of approximately 10° at the junction of the bottom surface of angled region 47 and the bottom surface of second region 46 of elongated body 41. Although, in a preferred embodiment, these two bend angles are achieved through curvature of portions elongated body 41, sharper bends, rather than more gentle curves, may alternatively be used.

First hook member 44 includes curved region 58, having an apex 54 and curving from first region 48 of elongated body 41, curving back upon the bottom surface of elongated body 41, back towards second end 43 and terminating in first pointed prong region 61. Similarly, second hook member 45 includes curved region 53, having an apex 59 and curving from first region 48 of elongated body 41, curving back upon the bottom surface of elongated body 41, back towards second end 43 and terminating in second pointed prong region 56. In a preferred embodiment of a six-hole hook plate of the present invention, wherein the instrument has an overall length of approximately 2.874 inches, and a length of elongated body 41 between first end 42 and second end 43 of approximately 2.278 inches, first prong region 61 and second prong region 56 both have a length of approximately 0.390 inches, as measured from apex to tip.

In the left offset plate, and as best seen in FIGS. 2B and 2D, hook plate 40 is not bilaterally symmetrical, relative to the longitudinal axis of elongated body 41. In particular, curved region 58 and its apex 54 of first hook member 44 is more distally spaced than curved region 53 and its apex 59, relative to both first end 42 and second end 43 of elongated body 41. In particular, in a preferred embodiment, apex 54 of first hook member 44 extends approximately 2 millimeters farther than apex 59 of second hook member 45, relative to second end 41 of elongated body 41. This asymmetrical configuration permits hook members 44 and 45, and hook plate 40 overall, to more closely approximate the often asymmetric contour of the distal surface of the fibula at the lateral malleolus, upon securement of hook plate 40 across the fracture site. In another embodiment, the surgeon is provided with a selection of plates in which the apex 54 of first hook 44 extends the same distance as the apex of 59 of the second hook member 45 (i.e., a bilaterally symmetrical hook plate); as well as a plate in which the apex 59 of second hook 45 extends 2 mm farther than the apex 54 of first hook 44 (i.e., a right offset plate). It can be seen by those skilled in the art that these variations can be values other than 2 mm and are intended to accommodate variability of the surface anatomy at the site of application.

Figure 2E:
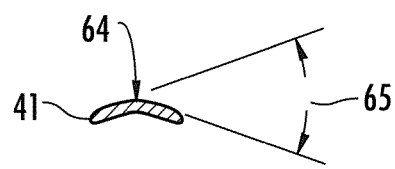
FIG. 2E is a sectional view of the 6-hole left offset fracture fixation plate, taken generally along lines 2E-2E of FIG. 2D.
Figure 2F:
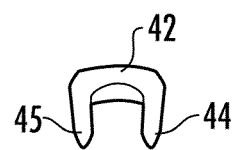
FIG. 2F is a front view of the 6-hole left offset fracture fixation plate.

As best seen in FIG. 2E, hook plate 40 has an arcuate cross section and bottom surface, along substantially all of the length of elongated body 41. This curved bottom surface permits hook plate 40 to more closely approximate the curved longitudinal surface of the fibula, upon securement of hook plate 40 across the fracture site.

Referring to FIG. 2C, prong region 56 of second hook member 45 has a longitudinal axis 55. Angled region 47 of elongated body 41 has a longitudinal axis 63. As shown in FIG. 2C, longitudinal axis 55 of second hook member 45 is substantially parallel to longitudinal axis 63 of angled region 47. Moreover, prong region 61 of first prong member 44 likewise has a longitudinal axis that is substantially parallel to longitudinal axis 63 of angled region 47. As explained in detail below, this parallel relationship is critical to allow hook plate 40 to seat congruently against the curved profile of the lateral malleolus as the hook members are impacted into a terminal fragment.

Figure 3A:
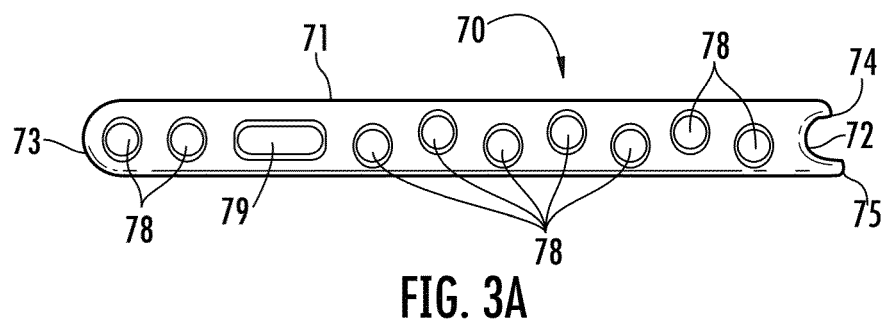
FIG. 3A is a top plan view of a 10-hole right offset fracture fixation plate of the present invention, configured for use in the fixation of certain fractures of the ankle.
Figure 3B:
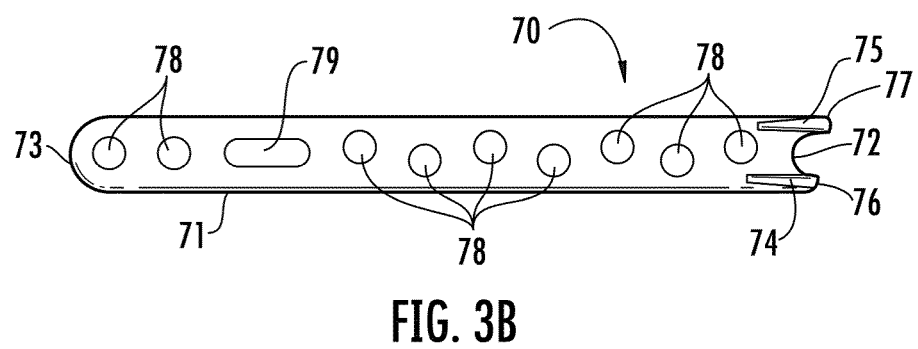
FIG. 3B is a bottom view of the 10-hole right offset fixation plate.

While, the example embodiment of the present invention shown in FIGS. 2A through 2F is configured for use in conjunction with fractures of the left fibula at the lateral malleolus, other configurations are also contemplated by the present invention. For example, FIGS. 3A and 3B show another, ten-hole embodiment of the present invention, configured for use in conjunction with fractures of the right lateral malleolus. Referring to FIGS. 3A and 3B, bone plate 70 is shown as comprising elongated body 71, having a first end 72 proximate first hook member, or tooth member 74 and second hook member, or tooth member 75, and a second end 75. Elongated body 71 includes a plurality of apertures therethrough for use in conjunction with conventional bone screws, including nine circular holes 78, and one slotted hole 79. First hook member 74 includes a first curved region having an apex 76. Second hook member 75 includes a curved region having an apex 77.

While bone plate 70 likewise displays bilateral asymmetry relative to its longitudinal axis, it is second hook member 75 having apex 77, on the right side of the bone plate, that is more distally spaced from first end 72 and second end 73 of elongated body 71. By way of contrast, in the previously described embodiment, it is first hook member 44 having apex 54, on the left side of the bone plate, that is more distally spaced from first end 42 and second end 43 of elongated body 41. This "mirror image" general configuration of bone plate 70, relative to bone plate 40, permits bone plate 70 to more closely approximate the curvilinear contoured distal surface of the right fibula at the lateral malleolus, upon securement of hook plate 70 across a fracture site.

Although both a six-hole left bone plate and a ten-hole right bone plate have been described above, other configurations of the present invention are also contemplated, including both left and right variations of bone plates, ranging in size from a four-hole bone plate, having an overall length of approximately 2.264 inches, to a twelve-hole bone plate, having an overall length of approximately 5.335 inches, or longer plates with more holes. Moreover, although, in preferred embodiments, each bone plate includes one slotted or oval hole for use in cooperation with bone screws, with the remaining holes being circular, other combinations of slotted and round bone screw accepting holes may alternatively be used. Alternatively, the hooks may be of identical length.

Figure 4:
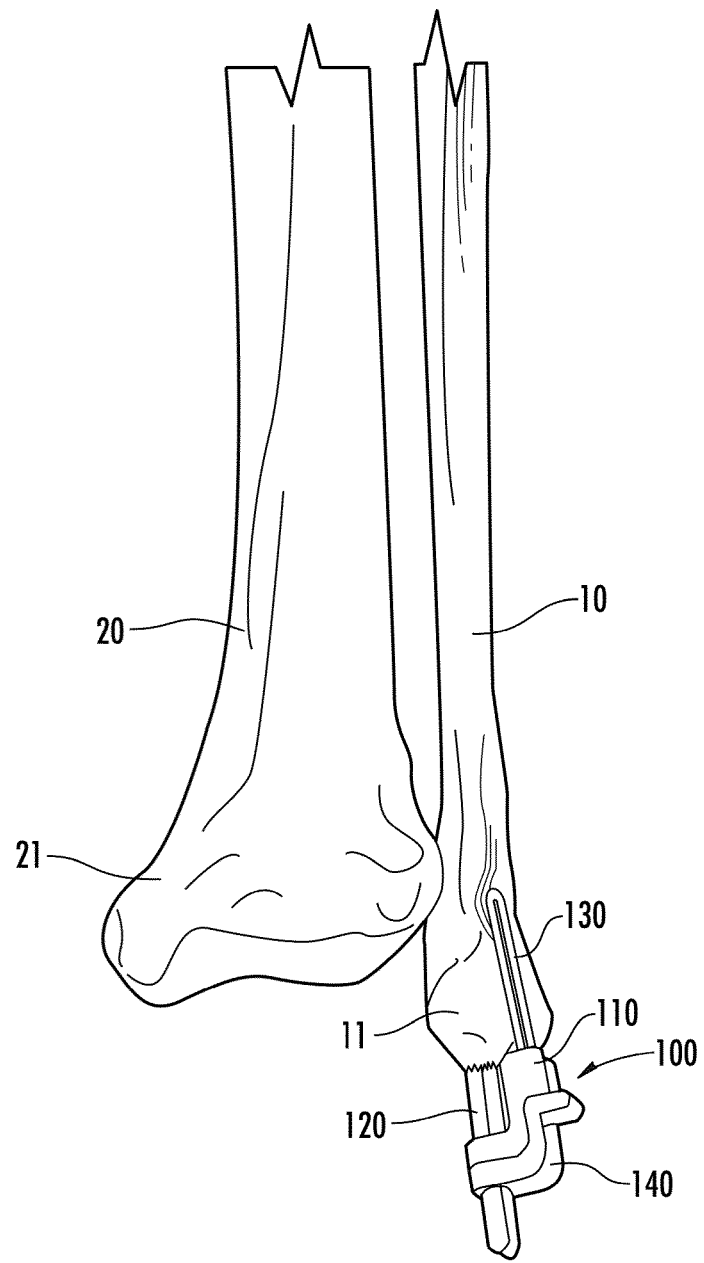
FIG. 4 is a perspective view of the double barreled drill guide of the present invention, shown positioned adjacent the lateral malleolus.
Figure 5:
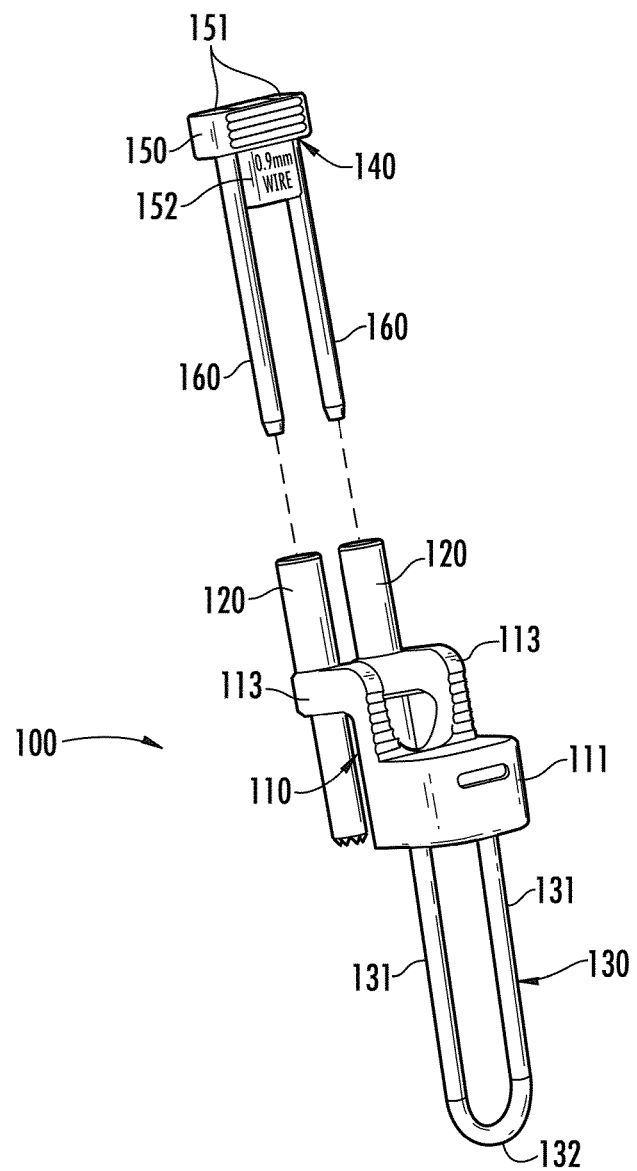
FIG. 5 is an exploded perspective view of the drill guide base assembly and interchangeable drill guide insert.

The present invention also comprises a double barreled drill guide, configured to direct a drill or K-wire in the proper depth and angle, relative to the lateral malleolus, such that, after pilot holes are drilled for the hook members and upon subsequently impacting the hook members of the present hook plate, the bottom surface of the hook plate tracks, and, when fully seated, is substantially adjacent, the surface contour of the lateral malleolus and the adjacent lateral surface of the fibula. The double barreled drill guide of the present invention is shown in FIGS. 4 and 5 as comprising drill guide base assembly 100. In addition, this guide may also be used with an interchangeable drill guide insert 140.

Figure 6:
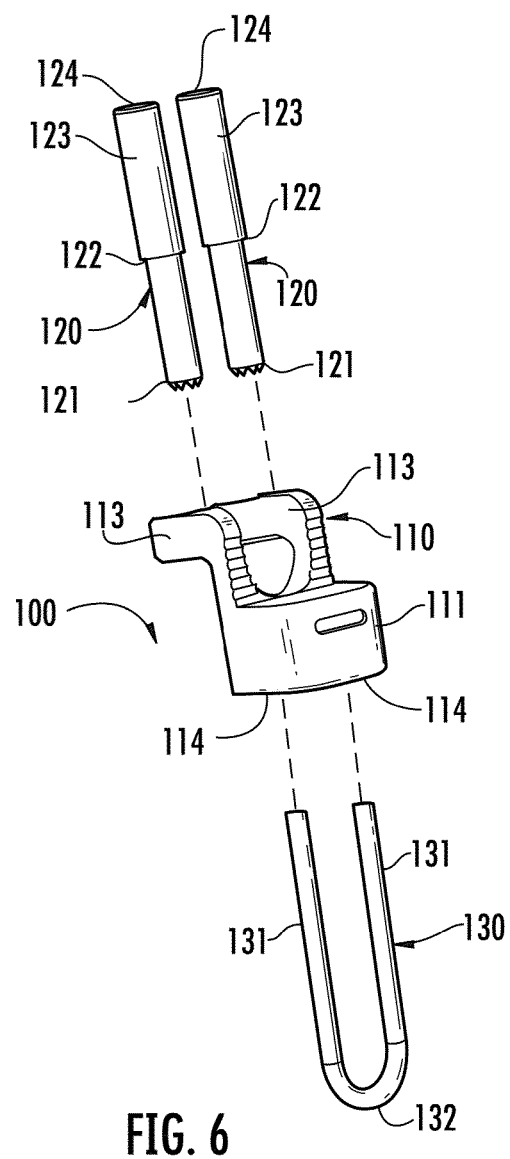
FIG. 6 is an exploded perspective view of the drill guide base assembly.
Figure 7A:
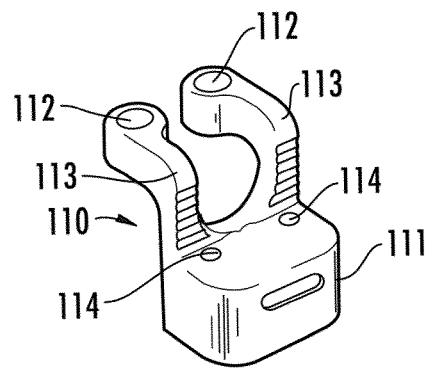
FIG. 7A is a perspective view of the body portion of the drill guide base assembly.
Figure 7B:
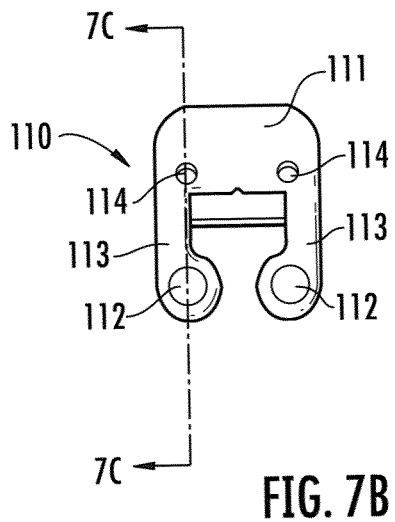
FIG. 7B is a back view of the body portion of the drill guide base assembly.
Figure 7C:
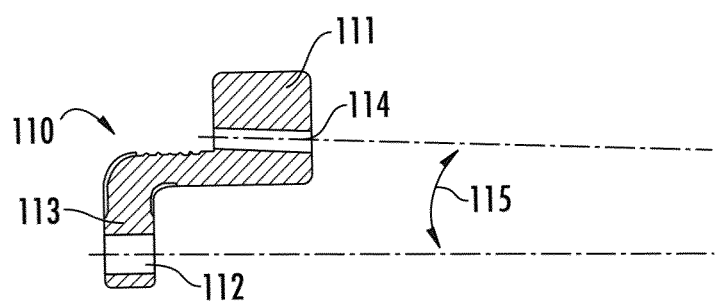
FIG. 7C is a sectional view of the body portion of the drill guide base assembly, taken generally along lines 7C-7C of FIG. 7B.

Drill guide base assembly 100 is shown in FIGS. 5 through 7C as comprising body portion 111, two base sleeves 120, and base positioning member 130. Body portion 111 has two apertures 114 extending therethrough, and two arm members 113, each having an associated aperture 112 extending therethrough. As shown in FIG. 7C, apertures 112 and 114 are canted slightly towards each other by a predetermined angle 115, relative to their respective longitudinal axes. In a preferred embodiment, predetermined angle 115 is a slight, acute approximately 3 degrees. This slight angle accounts for a certain amount of relative flex in the components of the drill guide and results in a substantially parallel alignment of the sleeves and the base positioning member upon application of the base positioning member against a superficial surface of the terminal end of the bone. In an alternative embodiment of the present invention, no predetermined angle 115 is employed, as the sleeves and base positioning member have longitudinal axes that are substantially parallel to each other. Upon assembly of drill guide base assembly 100, this, in turn, places each of base sleeves 120 at predetermined angle 115, canted towards base positioning member 130. This likewise places the sleeves of interchangeable drill guide insert 140 at a predetermined angle 115, canted towards base positioning member 130, upon insertion of the drill guide insert 140 into base assembly 100. As a result, the two pilot holes for the hook members of the present invention are drilled at predetermined angle 115, relative to base positioning member 130. Body portion 113 is preferably constructed of a surgical stainless steel material, such as type 303 surgical stainless steel.

Base sleeve 120 is shown in FIG. 6 as comprising a generally tubular body having a first end 121, shoulder 122, collar region 123, and second end. First end 121 has a chamfered and serrated configuration, permitting drill guide base assembly 100 to grip the distal surface of the lateral malleolus when positioned prior to drilling pilot holes for the hook members of the bone plate as shown in FIG. 4, serving to inhibit unwanted slippage of the overall drill guide. An internal channel communicates between openings at first end 121 and second end 122, and is sized to axially receive a drill. In a preferred embodiment, collar region 123 has a length of approximately 0.400 inches, and base sleeve 120 has an overall length of approximately 1.025 inches. Base sleeve 120 is preferably constructed of a surgical stainless steel material, such as type 455 surgical stainless steel, condition H-900.

As shown in FIG. 6, base positioning member 130 is substantially U-shaped, having two elongated arms 131 and U-shaped end 132. Base positioning member 130 is preferably constructed of a stainless steel material, such as type 316LS stainless steel having a minimum ultimate tensile strength of 160 KSI. In another embodiment, base positioning member 130 may be of the form of a plate having a contoured surface approximating the contoured elongated body of the bone plate to be implanted, or one or more pins (not shown).

Drill guide base assembly 100 is assembled by press fitting each base sleeve 120 though an associated aperture 112 of arm 113 of body portion 111, until shoulder 122 rests adjacent a top surface of arm 113. Base positioning member 130 is affixed to body portion 111 by inserting each elongated arm 131 through an associated aperture 114 of body portion 111, and then welding base positioning member in place using a nickel or other suitable braze.

Figure 8A:
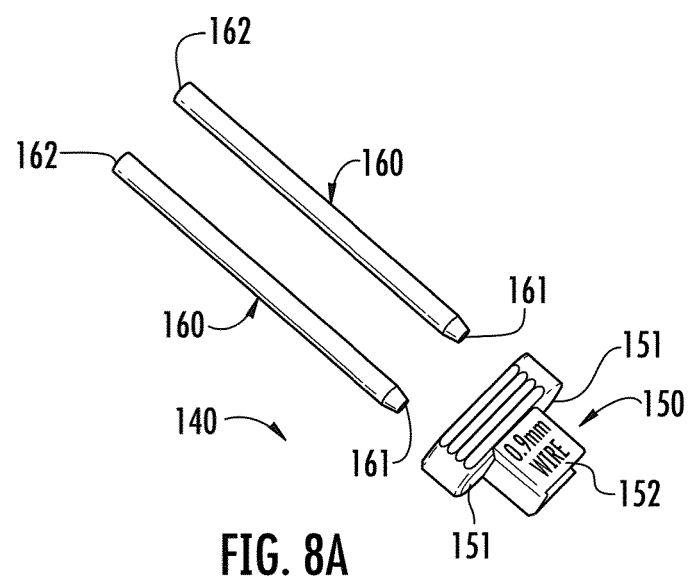
FIG. 8A is an exploded perspective view of the interchangeable guide wire insert.
Figure 8B:
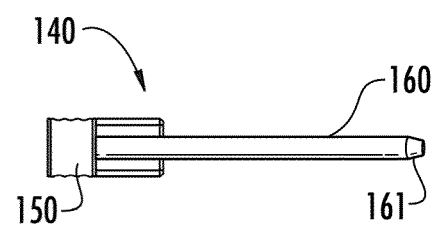
FIG. 8B is a side view of the interchangeable guide wire insert.

Interchangeable drill guide insert 140 is shown in FIGS. 8A and 8B as comprising generally T-shaped body 150 and two tubular insert sleeves 160. T-shaped body 150 includes two apertures 151 extending therethrough, each accepting an associated insert sleeve 160, which is assembled by press-fitting each inner sleeve 160 into an associated aperture 151. Two inwardly curving recesses extending along T-shaped body 150 have a radius of curvature coinciding with the exterior surface of collar region 123 of base sleeve 120 of drill guide base assembly 100, serving to further secure interchangeable drill guide insert 140 to drill guide base assembly 100, as tubular insert sleeves 160 are advanced within associated base sleeves 120 until T-shaped body 150 is fully seated adjacent body portion 111 of drill guide base assembly 100. T-shaped body 150 is preferably constructed of a surgical stainless steel material, such as type 303 surgical stainless steel.

Each insert sleeve 160 includes a tapered first end 161, second end 162, and an internal channel communicating between openings at first end 161 and second end 162. This internal channel is sized to accommodate a guide wire of a predetermined size, such as a 0.9 millimeter Kirshner wire, or K-wire, to be used in conjunction with a 2.0 mm cannulated drill that is subsequently guided over the wire upon removal of the double barreled drill guide, creating the pilot holes to accept axial impacting of the hook members of the present bone plate. This, in turn, gives the surgeon the option of either drilling holes directly into the terminal bone fragment using a non-cannulated drill by using guide assembly 100 without the insert 140, or, if less speed and greater potential precision is desired, to first insert a K-wire, and then pass a cannulated drill over the wire by using guide assembly 100 with insert 140. In a preferred embodiment of the present invention, insert sleeve 150 is approximately 1.150 inches in length. Insert sleeve 160 is preferably constructed of a surgical stainless steel material, such as type 455 surgical stainless steel, condition H-900.

As shown in FIG. 8A, T-shaped body 150 includes laser-etched indicia 152, indicating the size of guide wire accommodated by the present interchangeable drill guide insert 140, in this case a 0.9 millimeter guide wire. Moreover, as other interchangeable drill and guide wire inserts of varying sizes may alternatively be used, laser-etched indicia 152 is changed as necessary indicate the particular drill or guide wire size for each variation of interchangeable drill guide insert 140.

Figure 9A:
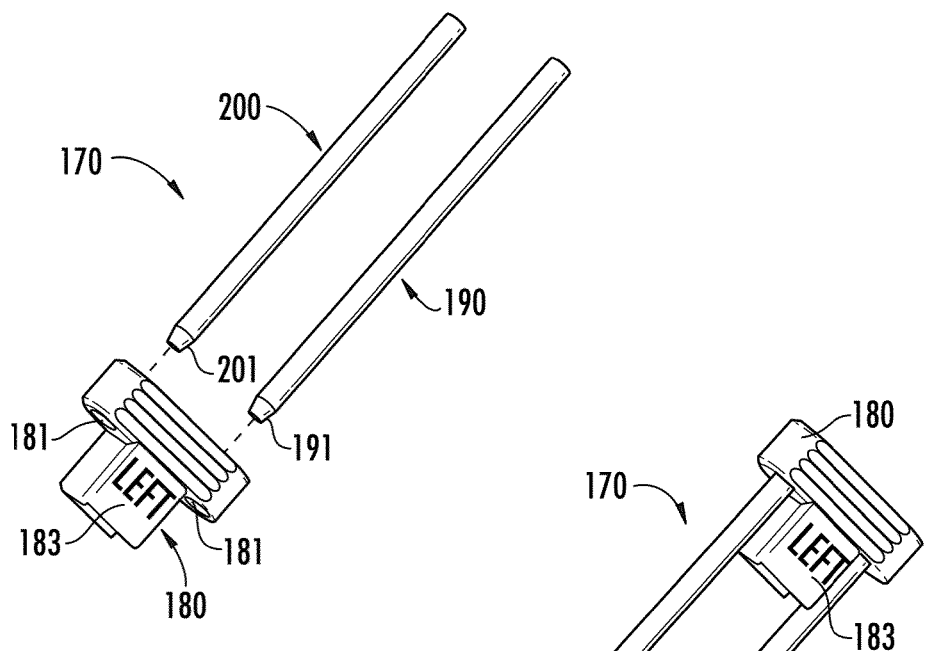
FIG. 9A is an exploded left perspective view of the gauge assembly.
Figure 9B:
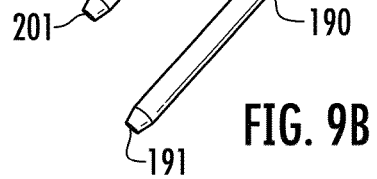
FIG. 9B is a left perspective view of the gauge assembly.
Figure 9C:
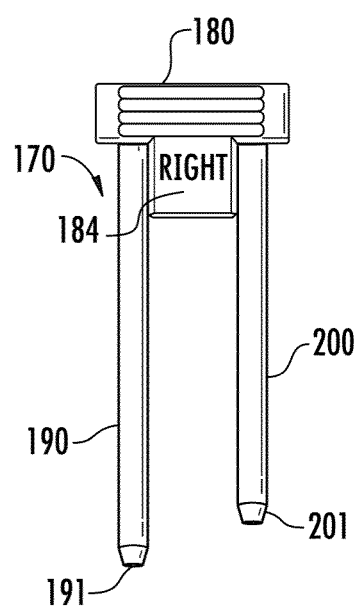
FIG. 9C is a top view of the gauge assembly.

In addition to releasably accepting interchangeable drill guide insert 140, drill guide base assembly 100 also releasably accepts a reversible gauge assembly 170, shown in FIGS. 9A through 9C as comprising T-shaped gauge body 180, first cylindrical elongated member, or trocar 190 having tapered end 191, and second cylindrical elongated member, or trocar 200 having tapered end 201. T-shaped body 180 includes two apertures 181 extending therethrough, each accepting an associated cylindrical trocar, and is assembled by press-fitting the trocars into associated apertures. Two inwardly curving recesses extending along T-shaped body 180 have a radius of curvature coinciding with the exterior surface of collar region 123 of base sleeve 120 of drill guide base assembly 100, serving to further secure gauge assembly 170 to drill guide base member 100, as cylindrical trocars 190 and 200 are advanced within associated base sleeves 120 until T-shaped body 180 is fully seated adjacent body portion 111 of drill guide base member 100. T-shaped body 180 further includes laser etched indicia 183 and 184, indicating "LEFT" and "RIGHT", respectively, on opposing sides of the T-shaped body. T-shaped body 180 is preferably constructed of a surgical stainless steel material, such as type 303 surgical stainless steel.

As shown in FIGS. 9A through 9C, first trocar 190 and second 200 are of different lengths, with first trocar 190 being longer than trocar 200. In a preferred embodiment, first trocar 190 is approximately 2 mm longer than second trocar 200, with first trocar being approximately 1.273 inches in length, and second trocar being approximately 1.150 inches in length. This differential permits a surgeon, prior to drilling any pilot holes, to use reversible gauge assembly 170 to confirm appropriate use of either a left or right offset hook plate of the present invention to properly accommodate the inclination of the bone curvature at the entry sites for the hooks and permit the hook plate to be properly seated adjacent the fibula upon impacting the hook members. In particular, once the double barreled drill guide is positioned adjacent the lateral malleolus as shown in FIG. 4, gauge assembly 170 is inserted into drill guide base assembly 100. Upon insertion, if the indicia 183 or 184 facing laterally, or outwardly is a correct indication of the left versus right offset hook plate to be used, the differential in lengths of trocars 190 and 200 will approximate the curvature of the lateral malleolus at the distal end of the fibula, and gauge assembly 170 will be substantially fully seated within base assembly 100. If, however, gauge assembly 170 does not substantially fully seat within base assembly 100, this is a visual indication that, since the differential in length of the trocars does not follow the contoured distal surface of the lateral malleolus, the indicia facing outwardly or laterally is most likely incorrect. In this case, the gauge assembly 170 can be withdrawn and flipped, and then reinserted to determine if the opposite offset hook plate is required. If the gauge assembly fully seats, it is indicative of the proper offset plate to use. If the gauge assembly does not seat when inserted with either attitude, it is indicative that a zero offset, bilaterally symmetrical plate is required.

Figure 10:
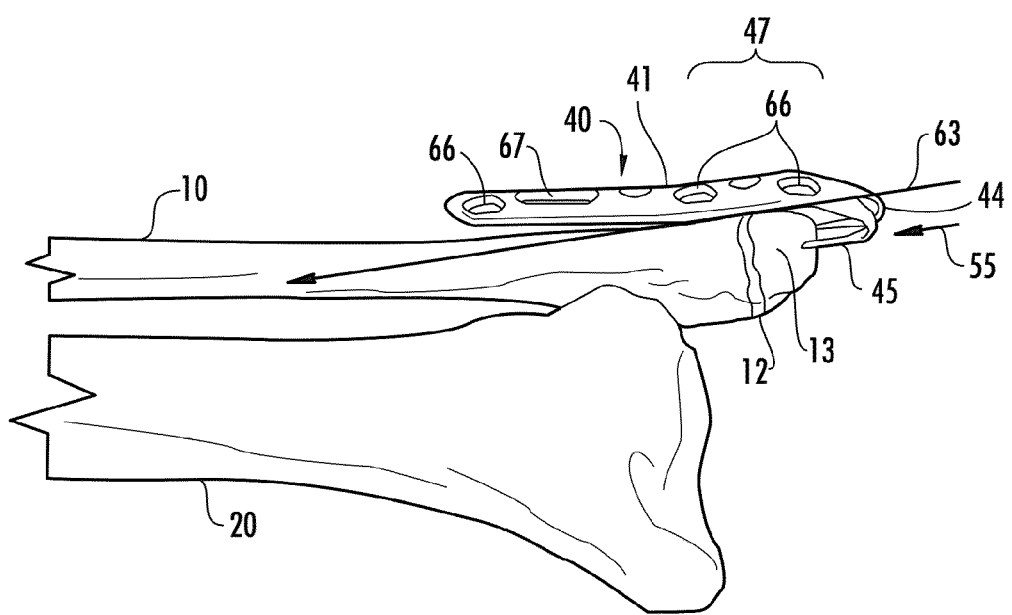
FIG. 10 is an anterior view, looking posteriorly, of the left tibia and fibula and showing, in particular, a 6-hole fracture fixation plate positioned immediately prior to impacting the hook members and affixation of the plate to the left fibula.
Figure 11:
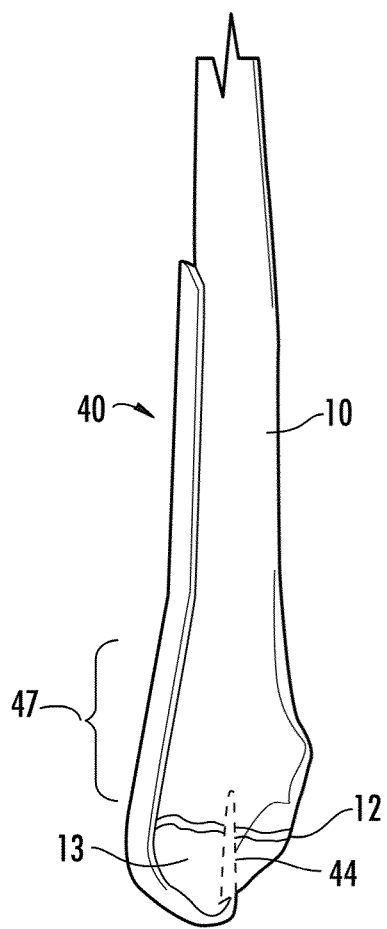
FIG. 11 is an anterior view of the right fibula showing, in particular, the positioning of the 6-hole fracture fixation plate following implantation and reduction of the fracture of the lateral malleolus in which the prong regions cross the fracture site.
Figure 12:
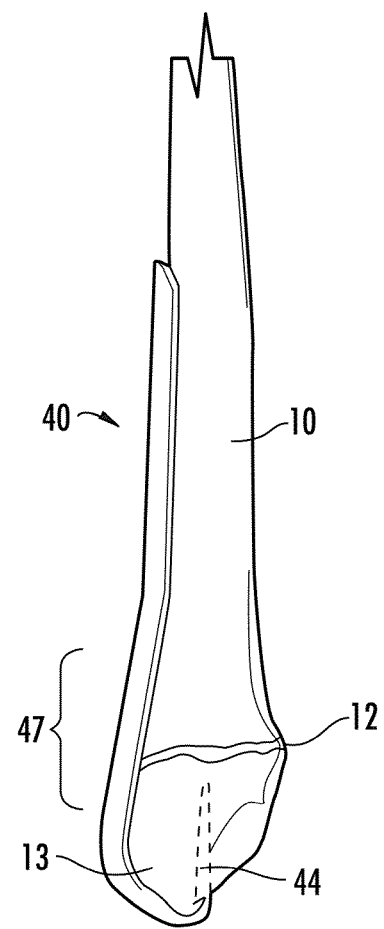
FIG. 12 is an anterior view of the right fibula showing, in particular, the positioning of the 6-hole fracture fixation plate following implantation and reduction of the fracture of the lateral malleolus in which the prong regions do not cross the fracture site.

As shown in FIG. 10, once the pilot holes are drilled using the double barreled drill guide (or once K-wires are positioned using the drill guide, and a cannulated drill is advanced over the wire to prepare the pilot holes), hook members 44 and 45 of hook plate 40 are longitudinally advanced into the pilot holes along longitudinal axis 55 of the hook members, using a hammer or other suitable instrument. Since the drill guide references the proper entry site and trajectory of the drill holes, impaction of the plate 40 into bone causes the plate to advance along longitudinal axis 63. When fully seated, first region 46, second region 48, and intermediate angled region 47 come to lie congruently along the curved surface of the bone. This anatomic fit of the plate against the bone is the result of designing the longitudinal axis 55 of the hooks to be parallel to the longitudinal axis 63 of the intermediate region 47, and to the creation of the specific entry site in the bone using the double barreled guide assembly 70 that matches the depth and trajectory of hooks 44 and 45. Following full axial insertion of the hook members, this, in turn, causes elongated body 41 of hook plate 40 to come to rest substantially adjacent the distal end of the fibula, with longitudinal axis 63 of angled region 47 substantially parallel to and coinciding with the flared end of the fibula at the lateral malleolus, as shown in FIGS. 11 and 12. Bone screws are then placed through appropriate circular and slotted holes of hook plate 40 and into the fibula, as desired, to secure hook plate 40 in place.

Although, as described above, a drill is used to prepare pilot holes in the lateral malleolus to receive the hook members, for patients with relatively soft bone, a surgeon may potentially opt to forego the preparation of pilot holes, and axially hammer the hook members of the bone plate of the present invention directly into place. Moreover, although the embodiment of the present invention discussed above is designed for use in conjunction with fractures of the lateral malleolus of the fibula, it may also be used in the configuration discussed above in conjunction with fractures of the medial malleolus of the tibia or other sites as discussed previously. Moreover, the overall lengths of the angled region, first region and second region of the elongated body, as well as the relative angles of the angled region with respect to the adjacent first and second regions of the elongated body, may be modified to more closely accommodate the terminal ends of other bones, such as the medial malleolus of the tibia, for the treatment of fractures thereof.

Figure 19:
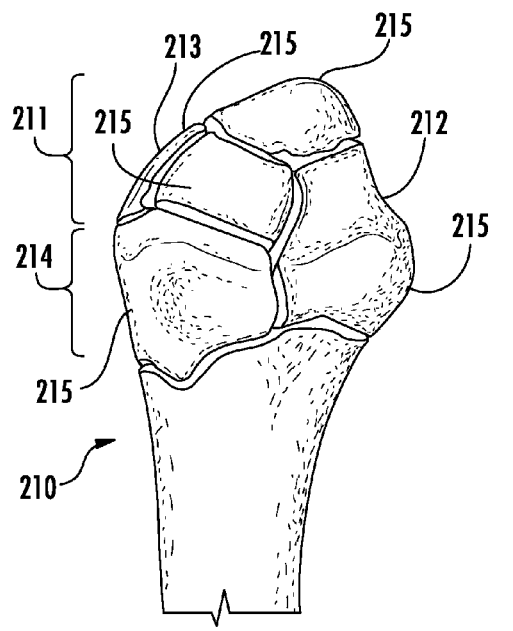
FIG. 19 is a medial view, looking laterally, of a fractured right radius and showing, in particular, several fragments of the volar rim and the dorsal rim.

A simplified medial view of a portion of a fractured right human distal radius 210 is shown in FIG. 19 as comprising distal radial epiphysis 211 including volar rim 212 and dorsal rim 213, and distal radial metaphysis 214. For illustrative purposes, distal radius 210 is shown having a plurality of fragments 215 associated with a fracture site.

A four-hole, neutral offset bone plate 220 of the present invention, configured for volar application in conjunction with fractures of distal radius, is shown in FIGS. 13A through 13E as comprising an elongated body 221, having a first end 222 proximate first hook member, or tooth member 224 and second hook member, or tooth member 225. Elongated body 221 includes a first region 228 proximate first end 222, a second region 226 proximate a second end 223, and an intermediate, angled, or "flared" region 227 disposed between first region 228 and second region 226. Elongated body 221 includes a plurality of apertures extending therethrough for use in conjunction with conventional locking or non-locking bone screws, including three circular holes 235, and one slotted hole 236. As best seen in FIGS. 13D and 13E, circular holes 235 and slotted hole 236 are substantially collinear in orientation. Alternatively, circular holes 235 may collectively have a staggered off-center orientation, relative to a longitudinal axis of elongated body 221, while slotted hole 236 may remain centered along this longitudinal axis. Moreover, and as best seen in FIG. 13A, slotted hole 236 and each circular hole 235 includes an associated countersunk, beveled perimeter, relative to the top surface of elongated body 221, facilitating the frusto-conical heads of conventional bone screws to be fully seated against, and hence in securing engagement with, an associated hole upon implantation. The countersunk, beveled perimeter of these apertures further serve to direct each associated bone screw into a desired orientation, typically substantially perpendicular to the adjacent portion of the contoured surface of elongated body 221.

As best seen in FIG. 13C, angled region 227 is generally defined and created by the presence of an angle of curvature 229 relative to the bottom surface of bone plate 220 proximate the juncture of substantially linear first region 228 and substantially linear angled, or flared region 227. The length of the linear angled region 227 and the inclination defined by the angle of curvature 229 substantially match the length and inclination of the flare of the associated bone requiring fracture fixation, in this case the radius, with volar application proximate the volar rim at the distal radial epiphyseal plate. It should be noted that substantially linear first region 228 may alternatively be a curved surface that may be approximated by a best fit inclination angle. As a result, the bottom surface of elongated body 221 of bone plate 220 is given an overall longitudinal contour which substantially corresponds to the flared profile of the distal end of the human radius proximate the volar rim.

In one preferred embodiment, the length, contour and relative angling of linear angled region 227, relative to first region 228 and second region 226, is designed to match the flare of the surface contour of the site of application using an electronically scanned or mathematical three-dimensional model of the site of application, such as the dorsal rim, volar rim, or radial arm of the distal radius as examples. In particular, a three-dimensional mathematical model of a particular bone having a flared surface region proximate its terminal end is created, using a three-dimensional scan of either an actual human bone or an artificial model of a human bone, or a three-dimensional model created entirely by computer. Computer aided drafting software is then used in conjunction with this three-dimensional mathematical model of the bone to create a bone plate of the present invention having a back surface profile of angled region 227, first region 228 and second region 226 such that, when the prong members are impacted proximate the terminal end of the bone, this back surface profile substantially corresponds to the adjacent flared contour of the bone, such that the bone plate rests substantially adjacent the bone.

Referring to FIG. 13C, in a preferred embodiment of a four-hole neutral volar hook plate of the present invention, flare angle 229 is approximately 25° in curvature. Moreover, first toothed member 224 and second toothed member 225 are each disposed at an angle 231, relative to a longitudinal axis of flared region 227, at an angle of approximately 50°. Although, in a preferred embodiment, these two bend angles are achieved through curvature of portions of hook plate 220, sharper bends, rather than more gentle curves, may alternatively be used.

Figure 20:
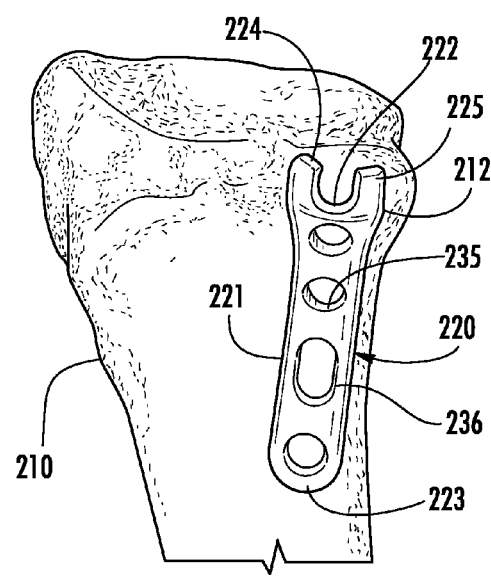
FIG. 20 is a top perspective view of the 4-hole, neutral offset fracture fixation plate of FIGS. 13A through 13E, shown impacted volarly into a fractured distal radius and prior to final affixation.
Figure 21:
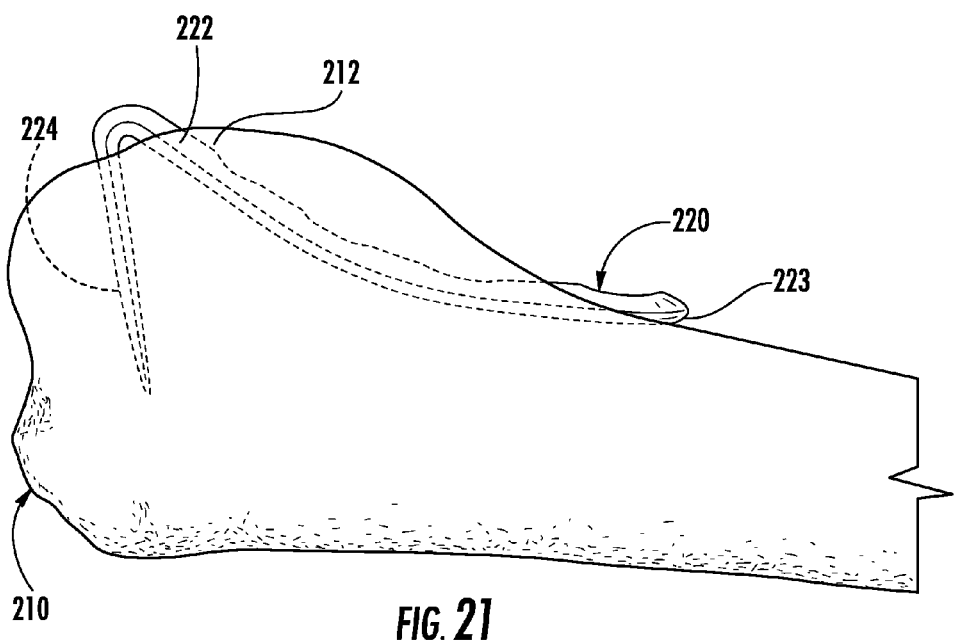
FIG. 21 is a medial view, looking laterally, of the distal radius and showing, in particular, a 4-hole, neutral offset fracture fixation plate of FIGS. 13A through 13E, configured for volar application and shown impacted volarly into a fractured distal radius and prior to final affixation.
Figure 23:
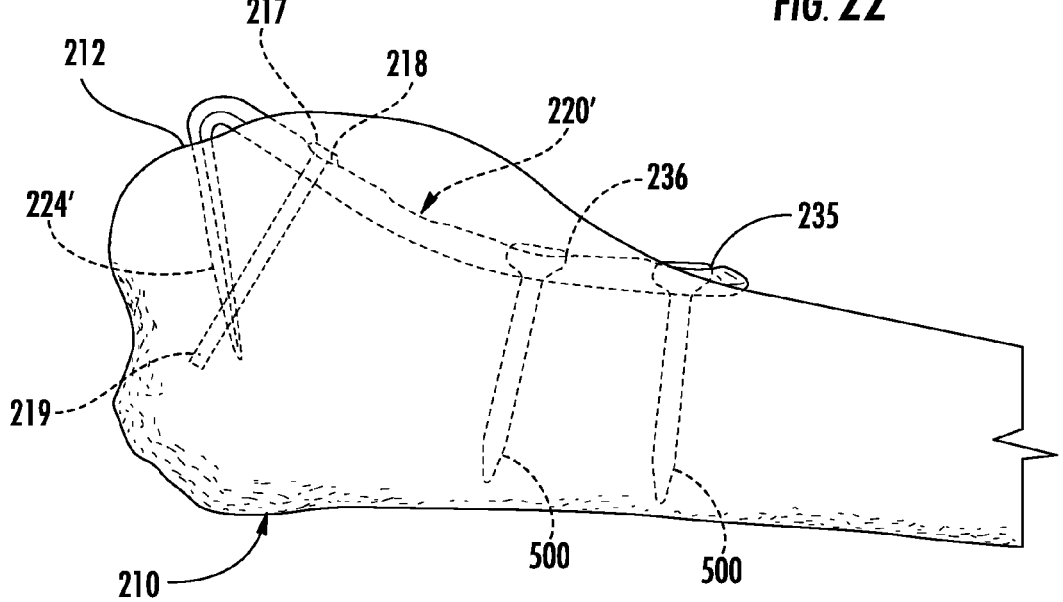
FIG. 23 is a medial view, looking laterally, of the distal radius and showing, in particular, a variation of the neutral offset fracture fixation plate of FIGS. 13A through 13E, configured for volar application with a locking peg and shown implanted for fixation of a fractured distal volar radius.
Figure 25:
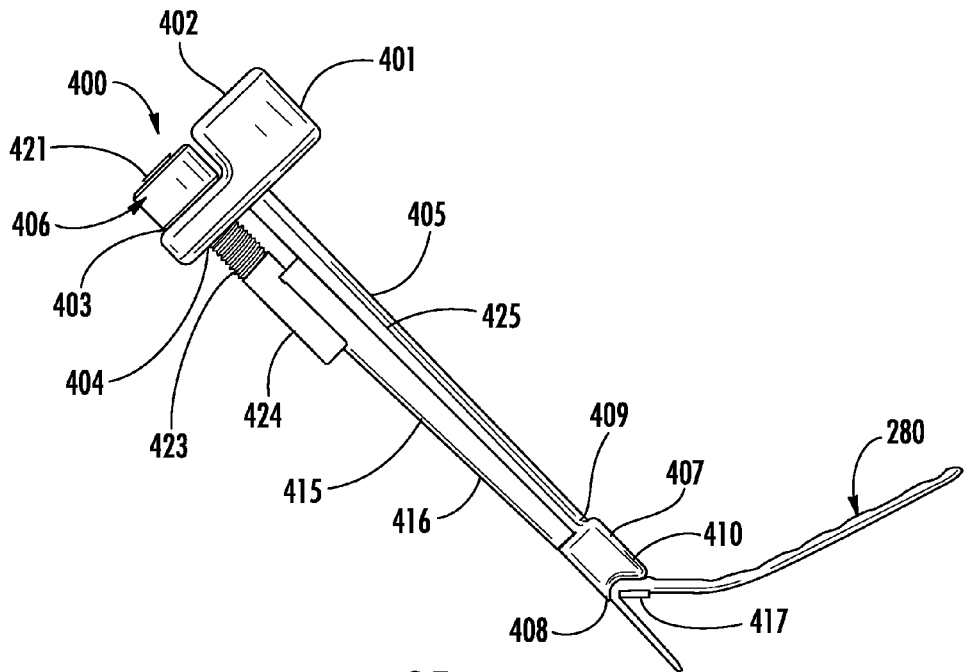
FIG. 25 is a left side view of a holder/impactor for use with the distal radius fracture fixation plates of the present invention, shown secured to the 7-hole, volar neutral offset fracture fixation plate of FIGS. 16A through 16C.
Figure 26:
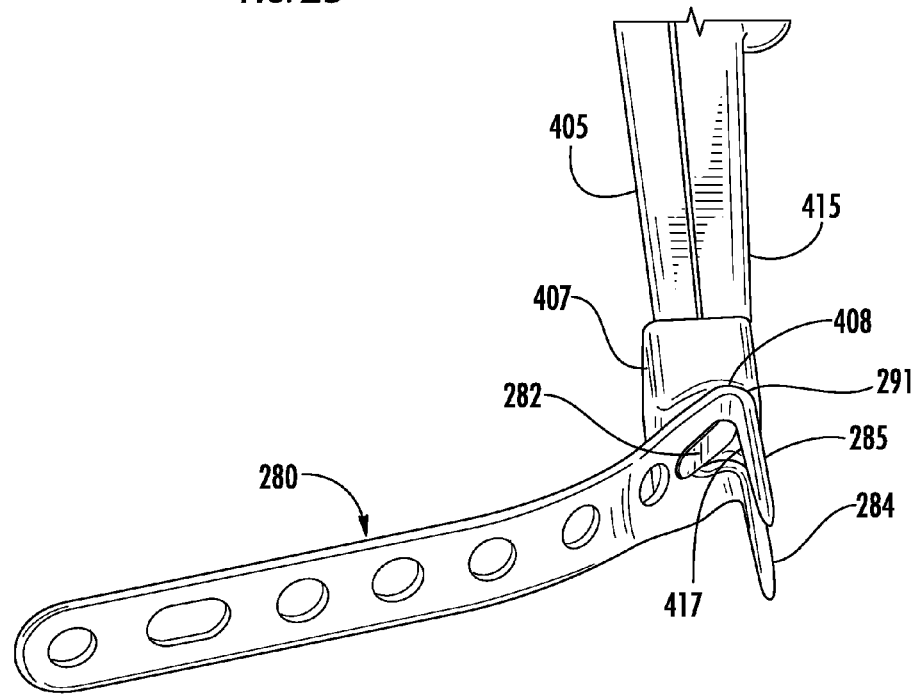
FIG. 26 is a bottom perspective view of the holder/impactor of FIG. 25, shown secured to a fracture fixation plate.

Bone plate 220 is shown in FIGS. 20 and 21 during implantation, impacted volarly into distal radius 210 adjacent volar rim 212 and prior to the placement of bone screws through holes 235 and 236. Next, as shown in FIG. 23, bone screws 500 are placed through one or more of holes 235 and 236 to secure bone plate 220 to the distal radius. For further enhanced securement, distal locking peg 219 is placed through a forward-most hole 217 which, in conjunction with countersunk aperture 218, directs distal locking peg to be positioned between first toothed member 224 and second toothed member 225.

Figure 14A:
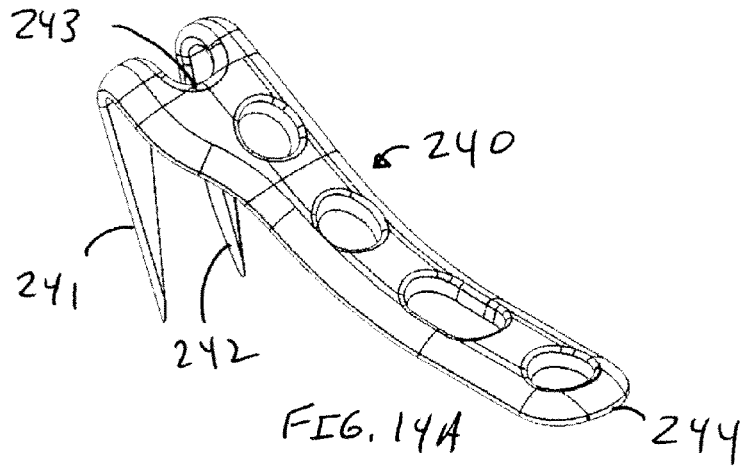
FIG. 14A is top perspective view of a 4-hole, left offset fracture fixation plate of the present invention, configured for volar application in the fixation of certain fractures of the distal radius.
Figure 14B:
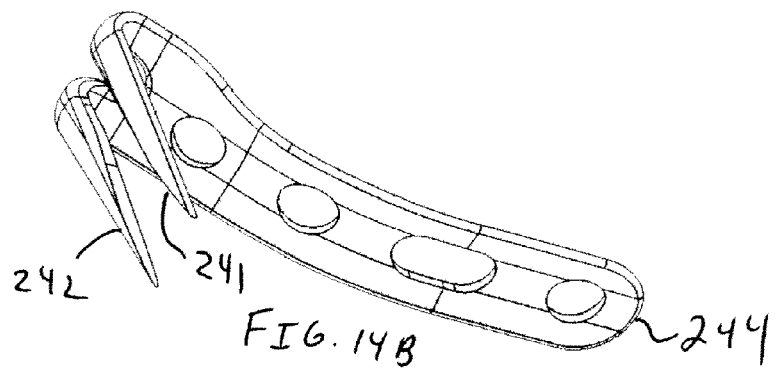
FIG. 14B is a bottom perspective view of the fracture fixation plate of FIG. 14A.
Figure 14C:
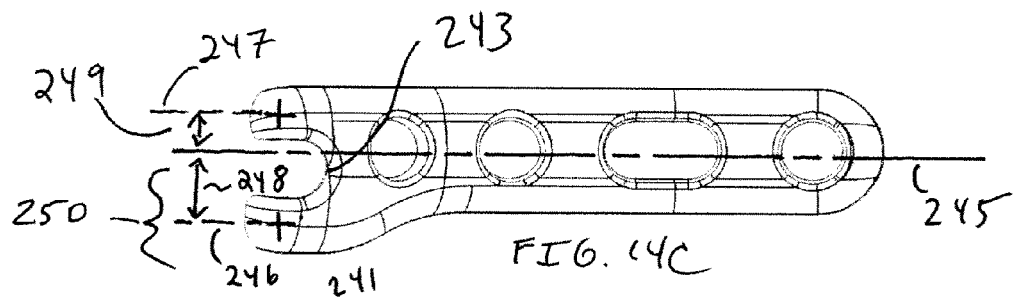
FIG. 14C is a top plan view of the fracture fixation plate of FIG. 14A.
Figure 14D:
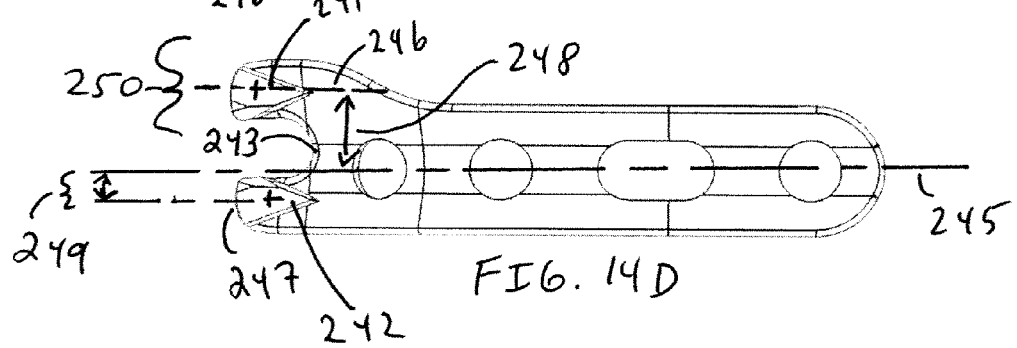
FIG. 14D is a bottom plan view of the fracture fixation plate of FIG. 14A.

A four-hole, left offset bone plate 240 of the present invention, configured for volar application in conjunction with fractures of distal radius, is shown in FIGS. 14A through 14D as comprising an elongated body having a first end 243 proximate first hook member, or tooth member 241 and second hook member, or tooth member 242, and a second end 244. In the left offset version, hook plate 240 is generally similar in configuration to hook plate 220, but is not bilaterally symmetrical, relative to the longitudinal central axis 245 of hook plate 240. In particular, as best seen in FIGS. 14C and 14D, a central vertical axis 246 of hook member 241 has a horizontal spacing 248 from longitudinal central axis 245 that is approximately twice that of horizontal spacing 249 of central vertical axis 247 from longitudinal central axis 245 of hook plate 240, yielding a larger left offset region 250. This asymmetrical configuration permits the selective use of left offset hook plate 240 in situations where use of neutral hook plate 220 would otherwise place a hook member through an undesired location of the distal radial fracture, such as at the juncture of a fragment, rather than through a fragment itself. It can be seen by those skilled in the art that variations in the left offset of the hook member other than twice the distance of the right hook member from the central longitudinal axis of the hook plate may alternatively be used.

A four-hole, right offset bone plate 260 of the present invention, configured for volar application in conjunction with fractures of distal radius, is shown in FIGS. 15A through 15D as comprising an elongated body having a first end 263 proximate first hook member, or tooth member 261 and second hook member, or tooth member 262, and a second end 264. In the right offset version, hook plate 260 is generally similar in configuration to hook plate 220, but is not bilaterally symmetrical, relative to the longitudinal central axis 265 of hook plate 260. In particular, as best seen in FIGS. 15C and 15D, a central vertical axis 267 of hook member 262 has a horizontal spacing 269 from longitudinal central axis 265 that is approximately twice that of horizontal spacing 268 of central vertical axis 266 from longitudinal central axis 265 of hook plate 260, yielding a larger right offset region 270. This asymmetrical configuration permits the selective use of right offset hook plate 240 in situations where use of neutral hook plate 220 or left offset hook plate 240 would otherwise place a hook member through an undesired location of the distal radial fracture, such as at the juncture of a fragment, rather than through a fragment itself. It can be seen by those skilled in the art that variations in the right offset of the hook member other than twice the distance of the right hook member from the central longitudinal axis of the hook plate may alternatively be used.

Figure 22:
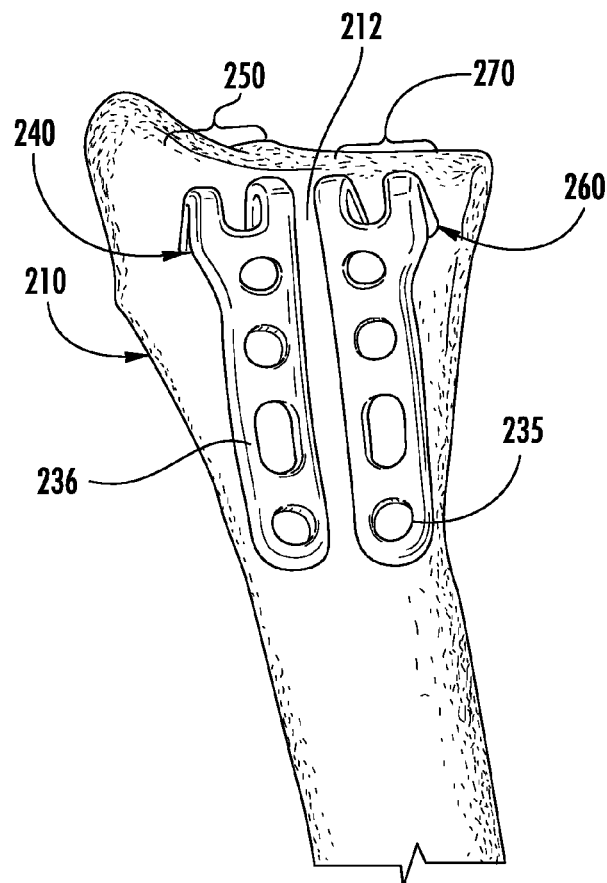
FIG. 22 is a top perspective view of the 4-hole, left offset fracture fixation plate of FIGS. 14A through 14D, as well as the 4-hole, right offset fracture fixation plate of FIGS. 15A through 15D, both shown impacted volarly into a fractured distal radius and prior to final affixation.

Left and right offset bone plates 240 and 260, respectively are shown in FIG. 22 during simultaneous implantation, impacted volarly into distal radius 210 in substantially parallel orientation adjacent volar rim 212 and prior to the placement of bone screws through holes 235 and 236. When so implanted, as shown in FIG. 22, left offset region 250 of bone plate 240 and right offset region 270 of bone plate 260 are disposed at opposing ends of volar rim 212.

Figure 16A:
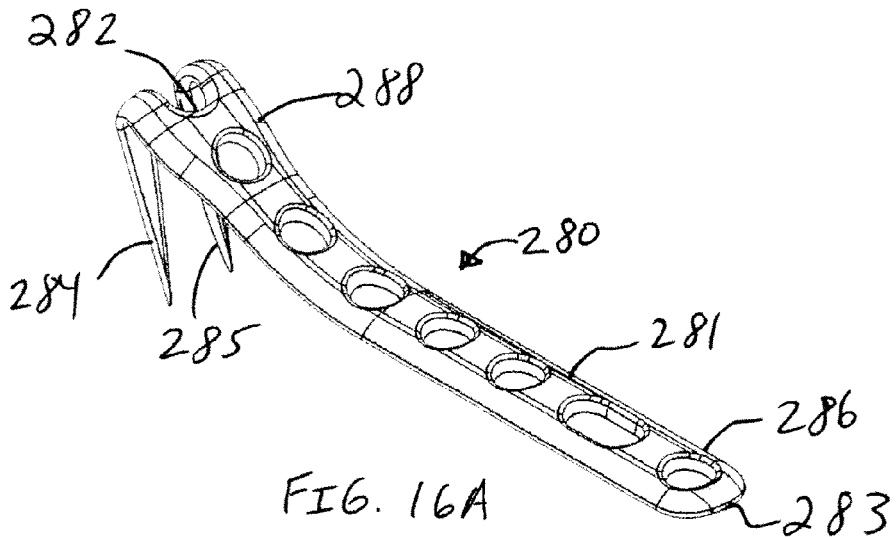
FIG. 16A is top perspective view of a 7-hole, neutral offset fracture fixation plate of the present invention, configured for volar application in the fixation of certain fractures of the distal radius.
Figure 16B:
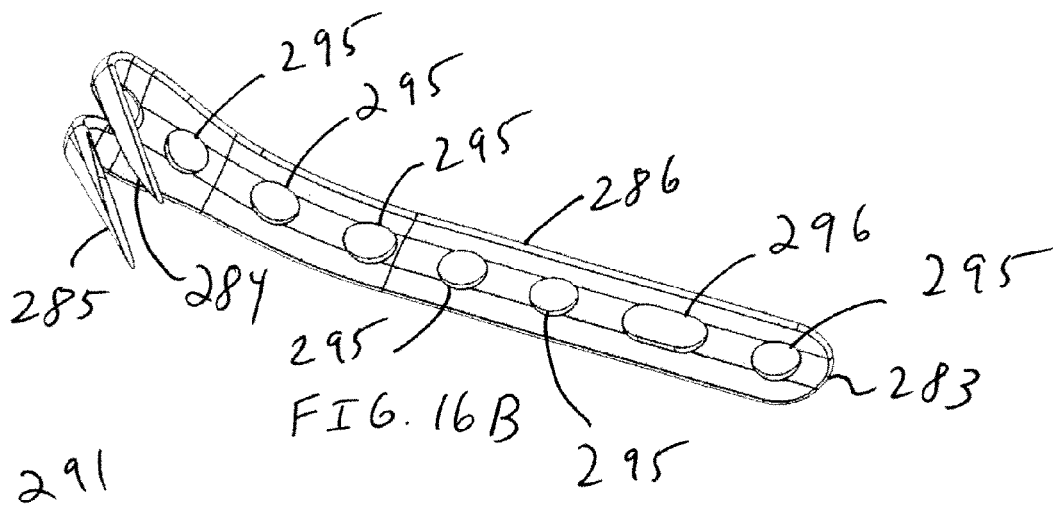
FIG. 16B is a bottom perspective view of the fracture fixation plate of FIG. 16A.
Figure 16C:
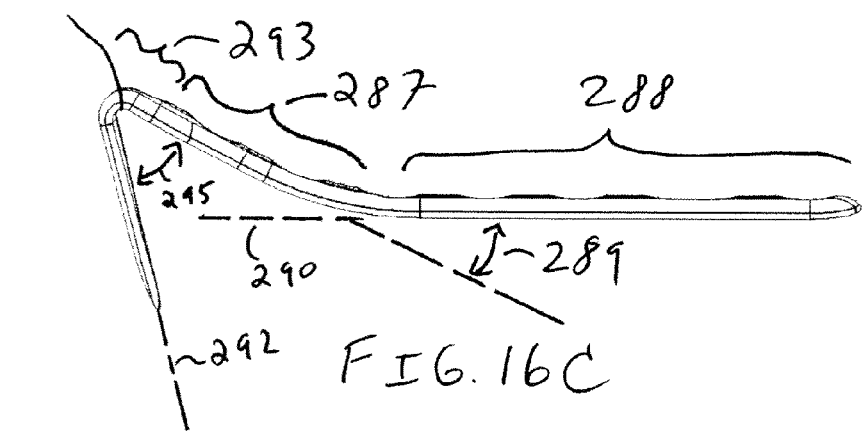
FIG. 16C is a left side view of the fracture fixation plate of FIG. 16A.

A seven-hole, neutral offset bone plate 280 of the present invention, configured for volar application in conjunction with fractures of distal radius, is shown in FIGS. 16A through 16C as comprising an elongated body 281, having a first end 282 proximate first hook member, or tooth member 284 and second hook member, or tooth member 285. Elongated body 281 includes a first region proximate first end 282, a second region proximate a second end 283, and an intermediate, angled, or "flared" region disposed between the first region and the second region. Elongated body 281 further includes a plurality of apertures extending therethrough for use in conjunction with conventional locking or non-locking bone screws, including six circular holes 295, and one slotted hole 296. Circular holes 295 and slotted hole 296 are substantially collinear in orientation. Alternatively, circular holes 295 may be collectively have a staggered off-center orientation, relative to a longitudinal axis of elongated body 281, while slotted hole 296 may remain centered along this longitudinal axis. Moreover, and as best seen in FIG. 16A, slotted hole 296 and each circular hole 295 includes an associated countersunk, beveled perimeter, relative to the top surface of elongated body 281, facilitating the frusto-conical heads of conventional bone screws to be fully seated against, and hence in securing engagement with, an associated hole upon implantation. The countersunk, beveled perimeter of these apertures further serve to direct each associated bone screw into a desired orientation, typically substantially perpendicular to the adjacent portion of the contoured surface of elongated body 281.

As best seen in FIG. 16C, angled, or flared region 287 proximate prong region 293 is generally defined and created by the presence of an angle of curvature 289 relative to the bottom surface of bone plate 280 proximate the juncture of substantially linear first region 288 and substantially linear angled, or flared region 287. The length of the linear angled region 287 and the inclination defined by the angle of curvature 289 substantially match the length and inclination of the flare of the associated bone requiring fracture fixation, in this case the radius, with volar application proximate the volar rim at the distal radial epiphyseal plate. It should be noted that substantially linear first region 288 or second region 287 may alternatively be a curved surface that may be approximated by a best fit inclination angle. As a result, the bottom surface of elongated body 286 of bone plate 280 is given an overall longitudinal contour which substantially corresponds to the flared profile of the distal end of the human radius proximate the volar rim.

Referring to FIG. 16C, in a preferred embodiment of a seven-hole neutral volar hook plate of the present invention, flare angle 289 is approximately 25° in curvature. Moreover, first toothed member 284 and second toothed member 285 are each disposed at an angle 295, relative to a longitudinal axis of flared region 287, at an angle of approximately 50°. Although, in a preferred embodiment, these two bend angles are achieved through curvature of portions of hook plate 280, sharper bends, rather than more gentle curves, may alternatively be used.

Figure 17A:
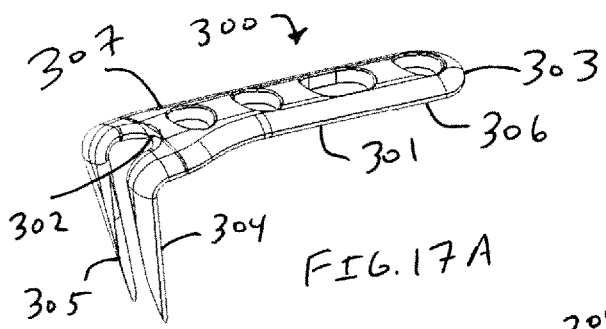
FIG. 17A is top perspective view of a 4-hole, neutral offset fracture fixation plate of the present invention, configured for dorsal application in the fixation of certain fractures of the distal radius.
Figure 17B:
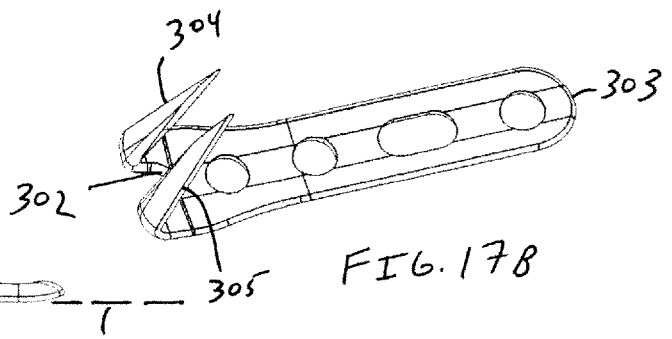
FIG. 17B is a bottom perspective view of the fracture fixation plate of FIG. 17A.
Figure 17C:
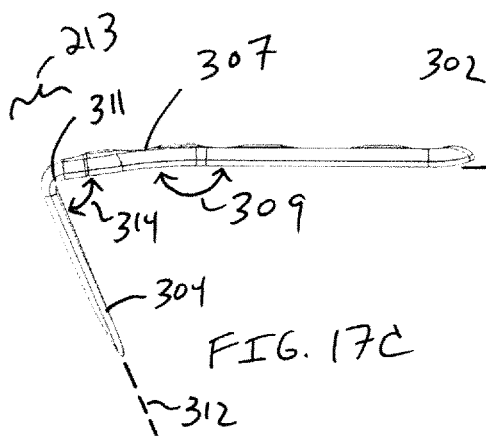
FIG. 17C is a left side view of the fracture fixation plate of FIG. 17A.
Figure 17D:
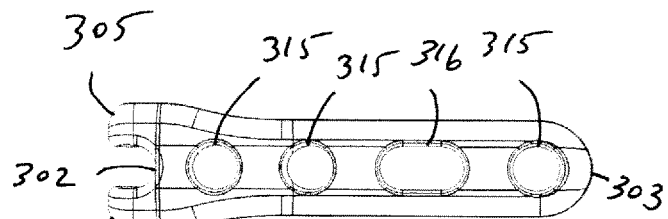
FIG. 17D is a top plan view of the fracture fixation plate of FIG. 17A.
Figure 17E:
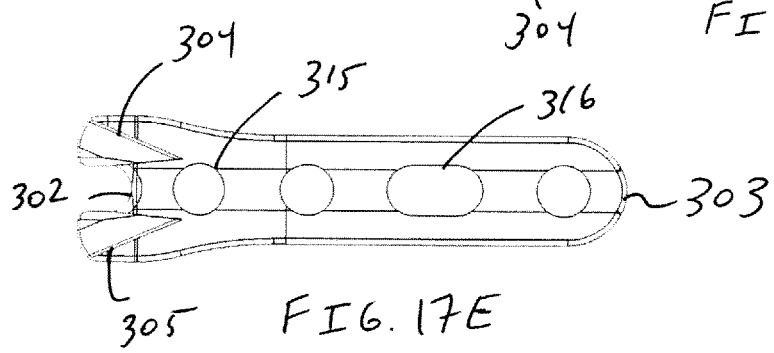
FIG. 17E is a bottom plan view of the fracture fixation plate of FIG. 17A.

A four-hole, neutral offset bone plate 300 of the present invention, configured for dorsal application in conjunction with fractures of distal radius, is shown in FIGS. 17A through 17E as comprising an elongated body 301, having a first end 302 proximate first hook member, or tooth member 304 and second hook member, or tooth member 305. Elongated body 301 includes a curved apex 311 proximate first end 302, a second region 306 proximate a second end 303, and an intermediate, angled, or "flared" region 307 disposed between curved apex 311 and second region 306. Elongated body 301 includes a plurality of apertures extending therethrough for use in conjunction with conventional locking or non-locking bone screws, including three circular holes 315, and one slotted hole 316. As best seen in FIGS. 17D and 17E, circular holes 315 and slotted hole 316 are substantially collinear in orientation. Alternatively, circular holes 316 may collectively have a staggered off-center orientation, relative to a longitudinal axis of elongated body 301, while slotted hole 316 may remain centered along this longitudinal axis. Moreover, and as best seen in FIG. 17A, slotted hole 316 and each circular hole 315 includes an associated countersunk, beveled perimeter, relative to the top surface of elongated body 301, facilitating the frusto-conical heads of conventional bone screws to be fully seated against, and hence in securing engagement with, an associated hole upon implantation. The countersunk, beveled perimeter of these apertures further serve to direct each associated bone screw into a desired orientation, typically substantially perpendicular to the adjacent portion of the contoured surface of elongated body 301.

As best seen in FIG. 17C, angled or flared region 307 is generally defined and created by the presence of an angle of curvature 309 relative to the bottom surface of bone plate 300 proximate the juncture of substantially linear first region 301 and substantially linear angled, or flared region 307. The length of the linear angled region 307 and the inclination defined by the angle of curvature 309 substantially match the length and inclination of the flare of the associated bone requiring fracture fixation, in this case the radius, with dorsal application proximate the dorsal rim at the distal radial epiphyseal plate. It should be noted that substantially linear first region 307 may alternatively be a curved surface that may be approximated by a best fit inclination angle. As a result, the bottom surface of elongated body 301 of bone plate 300 is given an overall longitudinal contour which substantially corresponds to the flared profile of the distal end of the human radius proximate the dorsal rim.

Referring to FIG. 17C, in a preferred embodiment of a four-hole neutral dorsal hook plate of the present invention, flare angle 309 is approximately 175° in curvature. Alternatively, this region may be straight with a flare angle 309 of 180°. Moreover, first toothed member 304 and second toothed member 305 are each disposed at an angle 314, relative to a longitudinal axis of flared region 307, at an angle of approximately 75°. Although, in a preferred embodiment, these two bend angles are achieved through curvature of portions of hook plate 300, sharper bends, rather than more gentle curves, may alternatively be used.

A longer, seven-hole neutral dorsal radial bone plate 450, generally similar in overall configuration to four-hole hook plate 300 described above, is shown in FIGS. 24A and 24B during implantation, impacted dorsally into distal radius 210 adjacent dorsal rim 213 and prior to the placement of bone screws through holes 455 and 456. As best seen in FIG. 24B, flare angle 459 closely accommodates the slightly curved surface of distal radius 210 adjacent dorsal rim 213, and both first toothed member 454 and second toothed member 455, at second end 452 of hook plate 450, are impacted into the cortical bone region of the distal radius, in a direction generally transverse to a longitudinal axis of the distal radius, proximate the metaphyseal region. It should be noted that first toothed member 454 and second toothed member 455 provide support behind the dorsal sub-articular bone.

Figure 18:
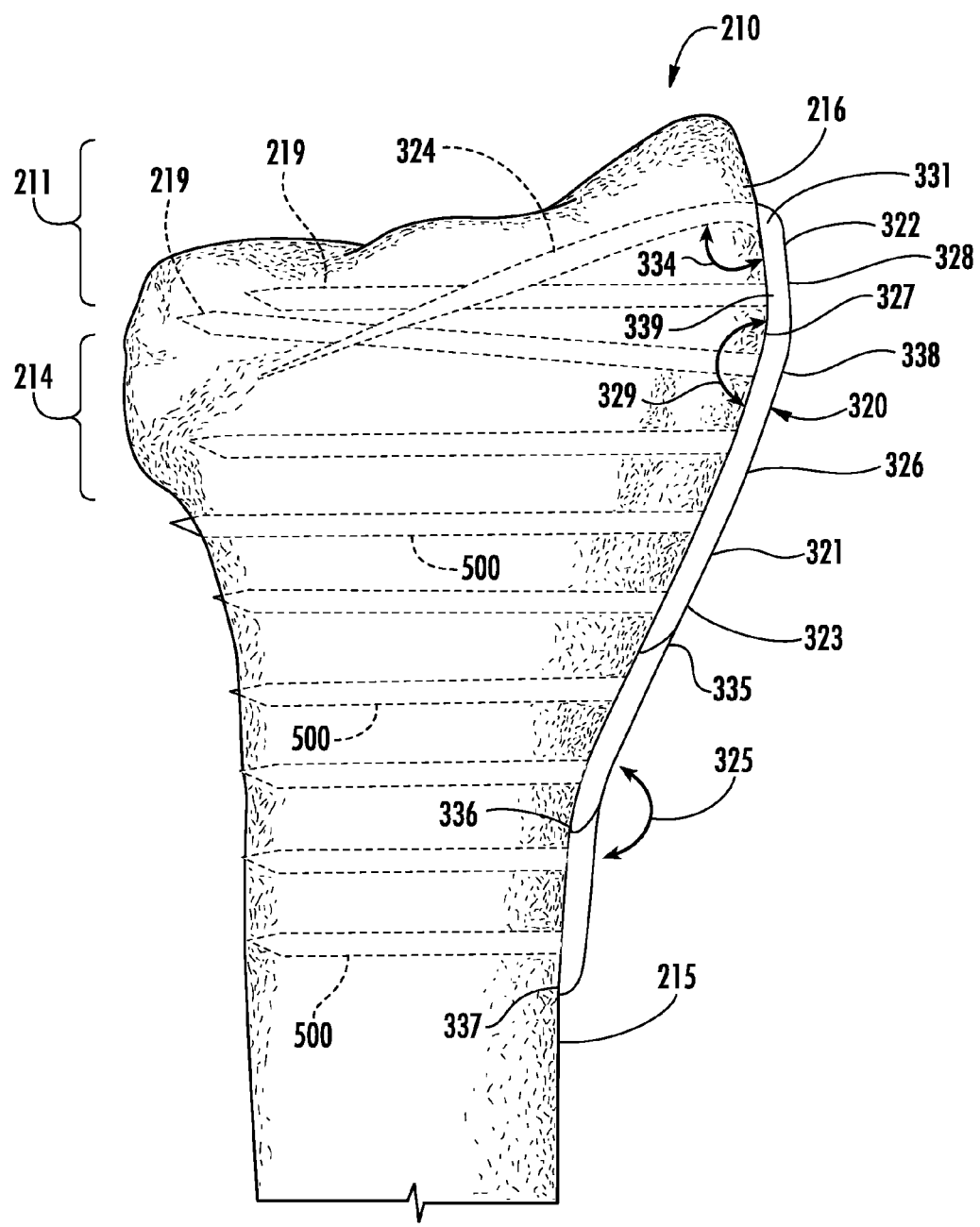
FIG. 18 is a dorsal view, looking palmarly, of the left radius and showing, in particular, the positioning of a 3-hole, 5-hole, or 7-hole, neutral offset fracture fixation plate of the present invention, configured for radial column application in the fixation for certain fractures of the distal radius, following implantation and reduction of a fracture.

A three, five or seven-hole, neutral offset bone plate 320 of the present invention, configured for radial arm application in conjunction with fractures of distal radius, is shown in FIG. 18 following implantation and reduction of such a fracture, as comprising an elongated body 321, having a first end 322 proximate first hook member, or toothed member 324 and a second hook member, or toothed member. Elongated body 321 includes a first region 328 proximate first end 322, a second region 326 proximate a second end 323, and an intermediate, angled, or "flared" region 327 disposed between first region 328 and second region 326. Elongated body 321 includes a plurality of apertures extending therethrough for use in conjunction with conventional bone screws 500. These may comprise a combination of circular and slotted holes, which may be substantially collinear in orientation, or which may collectively have a staggered off-center orientation, relative to a longitudinal axis of elongated body 321. Moreover, each slotted and circular hole includes an associated countersunk, beveled perimeter, relative to the top surface of elongated body 321, facilitating the frusto-conical heads of conventional bone screws to be fully seated against, and hence in securing engagement with, an associated hole upon implantation. The countersunk, beveled perimeters of these apertures further serve to direct each associated bone screw into a desired orientation, relative to the adjacent portion of the contoured surface of elongated body 321.

As shown in FIG. 18, elongated body 321 includes holes 338 and 339, each accommodating an associated distal locking peg 219. Each distal locking peg 219 extends through the gap between the first and second toothed members of hook plate 320.

Moreover, as shown in FIG. 18, hook plate 320 may be constructed of various lengths, such as, for example, a 3-hole hook plate terminating at second end 335; a 5-hole hook plate terminating at second end 336; or a 7-hole hook plate terminating a second end 337. In the example of a 7-hole hook plate, to accommodate the curvilinear surface of the radial arm of the distal radius, a second flare angle 325 is added to elongated body 326 of hook plate 320. In a preferred embodiment, second flare angle 325 may be approximately 160° in curvature.

For all of the above-described variations of hook plates of the present invention contoured for application to fractures of the distal radius, the first and second toothed members, which are substantially triangular in cross-section, are each preferably sharpened at the tip and along at least one of the vertical edges to create sharp cutting surfaces. This, in turn, permits each of these hook plates to be impacted at the fracture site without the need to pre-drill pilot holes to accept the toothed members, or tines of the hook plates. Instead, a holder/impactor may be used to securely hold the hook plate as it is first placed into an appropriate position adjacent the fracture, and then impacted into place by driving the hook members through the epiphyseal region of the distal radius. The use of a holder/impactor increases the simplicity of engaging the hooks into bone and the precision of accurate placement of the plate by the surgeon.

The present invention also comprises a combination holding and compacting instrument capable of both gripping a distal radius hook plate, and facilitating the impacting of the implant into distal bone fragments at the fracture site, without the need to pre-drill any pilot holes for the toothed members of the hook plate. In preferred embodiments, this instrument is attachable to and securely holds the hook plate proximate the first end, at the U-shaped juncture of the first and second toothed members, or times. Moreover, this instrument may preferably include a striking surface for receiving taps or blows from a surgical mallet or hammer, permitting a bone plate held by the instrument and suitably positioned to be directly impacted into the distal bone fragments. Moreover, although, in preferred embodiments, a combination holding and impacting instruments are disclosed, the holding and impacting of the hook plates of the present invention may alternatively be accomplished through the use of a first dedicated gripping instrument and a second dedicated impacting instrument.

A holder/impactor 400 for gripping and impacting the volar, dorsal, and radial arm distal radius hook plates of the present invention is shown in FIGS. 25 through 30 as comprising head member 401, having striking surface 402 and flanged region 403. Rigid elongated rod 405 couples head member 401, at one end, to distal housing 407, at an opposing end of rod 405. As best seen in FIGS. 27 and 30, distal housing 407 includes a contoured bottom surface 408, having a curvilinear form shaped to approximate the top surface of a distal radial hook plate of the present invention, such as 7-hole neutral volar hook plate 280, adjacent the top surface of the hook plate and proximate first end 282, proximate the substantially U-shaped junction of first tooth member 284 and second tooth member 285. Distal housing 407 further includes top aperture 410, permitting the axial movement of a portion of sliding shaft 415 therethrough, and shaped to accommodate the cross-section of sliding shaft 415, including guide rail 419, which is disposed longitudinally on one side of sliding shaft 415. Distal housing 407 also includes bottom slot 410, permitting the axial movement of foot member 47 and cylindrical riser 418 of sliding shaft 415 therethrough.

Sliding shaft 415 further includes tongue 416, which is disposed longitudinally on an opposing side of shaft 415, relative to guide rail 419, and runs along substantially the entire length of sliding shaft 415. Tongue 416 is inserted within and slidably engages groove 420 of elongated rod 405, which runs along substantially the entire length of rod 405.

Adjuster 402 adjusts the vertical position of sliding shaft 415 along and adjacent to elongated rod 405 and distal housing 407, and comprises adjustment knob 421 and adjustment shaft 422, having threaded top portion 423 and bottom portion 424, which is rigidly affixed to sliding shaft 415. Adjustment knob 421 threadedly engages adjustment shaft 422 and is positioned adjacent flanged region 403 of head member 401. Adjustment shaft 422 extends through an associated aperture 404 of flanged region 401. Bottom portion 424 of adjustment shaft 422 adjoins sliding shaft 415, and screws or other fastening means may be employed to affix adjustment shaft 422 of adjuster 402 to sliding shaft 415. Accordingly, as adjustment knob 421 is rotated in a first direction, its threaded engagement with threaded top portion 423 of shaft 422 imparts axial downward movement of shaft 422, in the direction towards distal housing 407. This, in turn, pushes sliding shaft 415 downward, causing foot member 417 and cylindrical riser 418 at the distal end of sliding shaft 415 to be extended through bottom aperture 410 of distal housing 407. Likewise, as adjustment knob 421 is rotated in a second, opposing direction, its threaded engagement with threaded top portion 423 of shaft 422 imparts axial upwards movement of shaft 422, in the direction away from distal housing 407. This, in turn, pulls sliding shaft 415 back upwards, causing foot member 417 and cylindrical riser 418 at the distal end of sliding shaft 415 to be retracted back through bottom aperture 410 of distal housing 407.

As shown in FIGS. 25, 26, 28, 29 and 30, this back- and forth rotation of knob 421 permits hook plate 280 to be securely gripped by holder/impactor 400. First, knob 421 is rotated in the first direction to extend foot member 417 and cylindrical riser 418 from distal housing 407. Next, holder/impactor 400 is fitted to hook plate 280, by placing contoured bottom surface 408 of distal housing 407 adjacent the top surface of hook plate 280 at first end 282. At the same time, foot member 417 is placed adjacent the bottom surface of hook plate 280 at first end 282, with cylindrical riser 418 nestled adjacent the U-shaped region between first toothed member 284 and second toothed member 285. Knob 421 is then rotated in the second direction, retracting food member 417 and cylindrical riser 418 towards distal housing 407. This, in turn, causes hook plate 280 to be securely gripped by holder/impactor 400, with first end 282 of hook plate 280 sandwiched between foot member 417 on the bottom and contoured bottom surface 408 of distal housing 407 on top, and with the abutment of cylindrical riser 418 and the U-shaped region between the toothed members of hook plate 420 further serving to tightly retain hook member 420 in place.

Next, hook plate 420 is positioned volarly, proximate a fracture of the volar rim of the distal radius. For other varieties of the distal radius hook plates of the present invention, the hook plate may be placed dorsally, or alongside the radial arm of the distal radius. A suitable surgical mallet or hammer is then employed to repeatedly tap or hit striking surface 402 of head member 401 to, in turn, drive toothed members 284 and 285 of hook plate 280 into the distal radius, including into distal bone fragments at the fracture site. Notably, upon attachment to a hook plate, elongated rod 405 is substantially collinear with the longitudinal axes of the toothed members of the hook plate. Accordingly, the force of taps or blows given to striking surface 402 are directed through elongated rod 405 and distal housing 407 to, in turn, provide an impacting force at the fracture site substantially along the longitudinal axes of the toothed members being impacted into the distal fragments. Hook plate 280 is preferably impacted most, but not all of the way in place in this manner, leaving enough room beneath the bottom surface of hook plate 280 for foot member 401 to be slightly extended away from distal housing 407 through the rotation of adjustment knob 401 in the first direction to, in turn, loosen the grip of holder/impactor 400 on hook member 280. Holder/impactor 400 is then removed, by drawing foot member 417 forward and away from hook plate 280, between toothed members 284 and 285. The surgical hammer or mallet, usually with a simple surface impactor, may then be employed to directly strike hook member 280, such as proximate first end 282, in order to complete the impaction of the hook plate. Suitable surgical screws and distal locking pegs may then be employed to fully reduce the fracture, and to secure hook plate 280 in place adjacent the distal radius at the fracture site.

Figure 31:
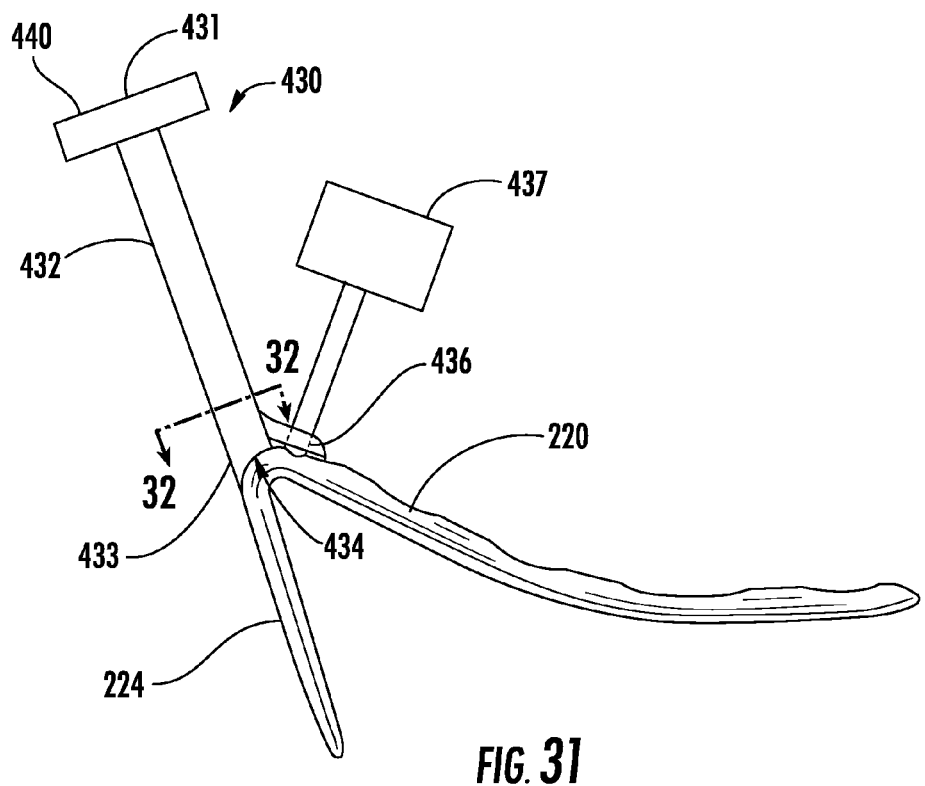
FIG. 31 is a left side view of another holder/impactor for use with the distal radius fracture fixation plates of the present invention, shown secured to the 4-hole, volar neutral offset fracture fixation plate of FIGS. 13A through 13E.
Figure 32:
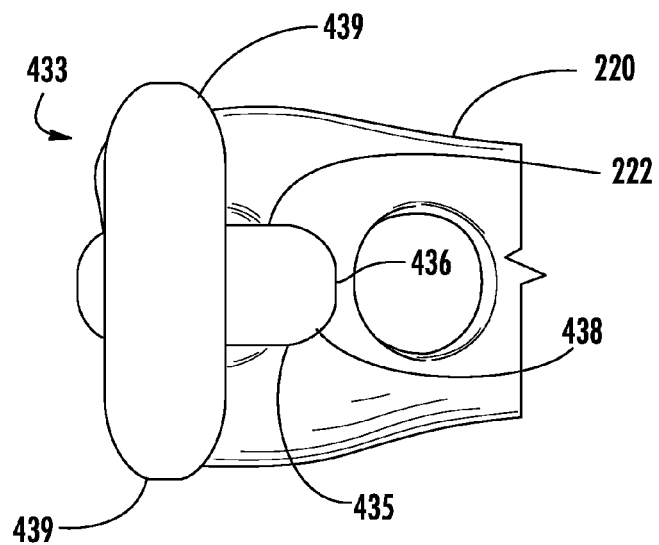
FIG. 32 is a top cross-sectional view of a portion of the distal gripping region of the holder/impactor of FIG. 31, taken generally along lines 32-32 of FIG. 31, shown secured to the 4-hole, volar neutral offset fracture fixation plate of FIGS. 13A through 13E.

Another embodiment of a holder/impactor 430 of the present invention is shown in FIGS. 31 and 32 as comprising head member 431 having striking surface 440, distal gripping region 433, and elongated shaft 432 connecting head member 431 and distal gripping region 433. Distal gripping region 433 includes bottom surface 434 that is contoured to approximate the contoured top surface of hook plate 220 to be implanted, proximate first end 222 of hook plate 220. Distal gripping region further includes a transverse slot 435, surrounded on both top and bottom surfaces by overhanging flanges 438, and threaded hole 436 disposed through the top overhanging flange 438. Locking thumbscrew 437 has a threaded distal region that threadedly engages female threads disposed within threaded hole 436 of distal gripping region 433.

To attach holder/impactor 430 to hook plate 220, a portion of distal gripping 433 region is inserted into the U-shaped region between the first and second toothed members at first end 222 of hook plate 220, with each tooth member overhanging region 439 overlying an associated toothed member. In this position, a portion of first end 222 of hook plate 220 is disposed within transverse slot 435, and is partially sandwiched between both top and bottom surfaces by overhanging flanges 438. Locking thumbscrew 437 is then tightened, such that a distal tip of thumbscrew 437 extends through the bottom surface of distal gripping region 433 and engages the top surface of hook plate 220, thereby biasing tooth member overhang regions 439 against corresponding top ends of associated toothed members, securing holder/impactor 430 to hook member 220.

A suitable surgical mallet or hammer is then employed to repeatedly tap or hit striking surface 440 of head member 431 to, in turn, drive the toothed members of hook plate 220 into the distal radius. Notably, upon attachment to a hook plate, elongated shaft 432 is substantially collinear with the longitudinal axes of the toothed members of the hook plate. Accordingly, the force of taps or blows given to striking 440 are directed through shaft 432 and distal gripping region 433 to, in turn, provide an impacting force at the fracture site substantially along the longitudinal axes of the toothed members being impacted into the distal fragments. Hook plate 220 is preferably impacted most, but not all of the way in place in this manner, leaving enough room beneath the bottom surface of hook plate 220 for bottom overhanging flange 438 to be slid away from underneath hook plate 220. Holder/impactor 430 is then removed, by first loosening thumbscrew 437, and the drawing distal gripping region 433 forward and away from hook plate 220, between the toothed members. The surgical hammer or mallet, typically with a simple surface impactor, may then be employed to directly strike hook member 220, such as proximate first end 222, in order to complete the impaction of the hook plate. Suitable surgical screws and distal locking pegs may then be employed to fully reduce the fracture, and to secure hook plate 220 in place adjacent the distal radius at the fracture site.

In preferred embodiments, the hook plates of the present invention may be constructed of wrought 18chromium-14nickel-2.5 molybdenum stainless steel, having a tensile strength of at least 135 Kips per square inch (KSI), and meeting the chemical and mechanical properties established by the ASTM-F139 standard. Other materials such as titanium, titanium alloy, or medical grade polymers may alternatively be used.

The present invention also comprises kits of combinations of the components described above. For example, a plurality of hook plates of multiple sizes, from four-hole to fifteen-hole embodiments in both left and right offset variations, and possibly with zero offset variations, may be provided in kit form so that appropriately sized and configured hook plates of the present invention are readily available at a hospital or trauma center. Moreover, one or more hook plates may be provided in kit form in combination with the double barreled drill guide and/or the holder/impactor of the present invention. Furthermore, the double barreled drill guide and/or the holder/impactor, either alone or as a part of a kit of one or more hook plates, may themselves be provided as a kit or sub-kit including the base assembly, interchangeable drill guides sized to accommodate guide wires and/or non-cannulated drills of varying sizes, and the gauge assembly.

Although the present invention has discussed plates with two hooks, it will be understood by those skilled in the art that other embodiments having one hook or a plurality of hooks are possible and do not depart from the scope or spirit of the present invention.

Although the present invention has shown two possible forms of a gripping and impacting instrument, it will be understood by those skilled in the art that these are provided as example and many variations of embodiments of instruments to rigidly grip and impact the plate are possible and do not depart from the scope or spirit of the present invention. For example, a gripping instrument, an impacting instrument, and/or a combination gripping and impacting instrument, may be configured to threadably engage a threaded hole of the bone plate, such as, for example, modifying the embodiment of FIGS. 31 and 32 to enlarge contoured bottom surface 434, such that locking thumbscrew 437 is directed into the threaded hole immediately adjacent first end 222 of bone plate 220. Moreover, the contoured bottom surface 434 of holder/impactor may be widened to overhang the side edges of a bone plate to, in turn, securely grip the bone plate by a portion of the side edges of the bone plate, proximate the toothed members. A snap-fit attachment may potentially be used. Alternatively, a forceps-like tensioner, integral with or operably coupled to the instrument, may operate as a "spreader", engaging the opposing inner surfaces of the toothed members at their U-shaped junction at first end 222 to, in turn, bias the overhanging side edges of the instrument against the side edges of the bone plate.

The preceding description and drawings merely explain the invention and the invention is not limited thereto, as those of ordinary skill in the art who have the present disclosure before them will be able to make changes and variations thereto without departing from the scope of the present invention.

What is claimed is:

1. An impacting instrument securely attachable to at least a portion of a bone plate, the bone plate having an elongated body having a first end, a second end, a top surface, a bottom surface, and at least two hook members disposed proximate the first end, the at least two hook members each having a prong region having a longitudinal axis, the impacting instrument comprising:
   a housing having a distal surface and a distal opening extending through the distal surface;
   an elongated shaft having a longitudinal axis, at least a portion of the elongated shaft being extendable through the distal opening;
   a foot member disposed at a distal end of the elongated shaft, the foot member having a longitudinal axis that is disposed at an oblique angle relative to the longitudinal axis of the elongated shaft;
   the distal surface of the housing has a surface contour comprising an elongated, substantially linear portion extending from one end, terminating in a substantially arcuate portion at an opposing end;
   the elongated shaft is substantially coaxial to the substantially arcuate portion of the surface contour of the distal surface of the housing;
wherein at least a portion of the bone plate is secured between at least a portion of the foot member and at least a portion of the distal surface of the housing upon attachment of the impacting instrument to the bone plate with the impacting instrument transferring force applied to a striking surface of the impacting instrument to the bone plate proximate the at least two hook members upon attachment of the impacting instrument to the bone plate.

2. The impacting instrument according to claim 1, wherein at least a portion of the impacting instrument has a surface contour matching at least a portion of a surface contour of the bone plate.

3. The impacting instrument according to claim 1, wherein the impacting instrument engages at least a portion of the top surface of the elongated body and at least a portion of the bottom surface of the elongated body.

4. The impacting instrument according to claim 1, wherein the force applied to the striking surface is transferred substantially collinearly to the longitudinal axes of the at least two hook members.

5. The impacting instrument according to claim 1, wherein the impacting instrument further includes an adjustment mechanism permitting adjustment of a gripping force applied to at least a portion of the bone plate by the impacting instrument.

6. The impacting instrument according to claim 1, wherein each of the at least two hook members is sharpened at a distal tip, permitting the at least two hook members to be impacted through a cortical bone region of a bone fracture site without drilling a pilot hole into the cortical bone region.

7. The impacting instrument according to claim 1, wherein each prong region has at least one longitudinal edge extending along at least a portion thereof, and wherein each hook member is sharpened along at least a portion of its at least one longitudinal edge, permitting each hook member to be impacted through a cortical bone region of a bone fracture site without drilling a pilot hole into the cortical bone region.

8. The impacting instrument according to claim 1, wherein the bone plate is configured for fixing fractures having at least one small terminal fragment of the distal radius.

9. The impacting instrument according to claim 1, wherein the foot member and the housing are substantially prohibited from rotating relative to each other.

* * * * *